US008377682B2

(12) United States Patent
Hartmann et al.

(10) Patent No.: US 8,377,682 B2
(45) Date of Patent: Feb. 19, 2013

(54) SYSTEM FOR THE HETEROLOGOUS EXPRESSION OF A VIRAL PROTEIN IN A CILIATE HOST CELL

(75) Inventors: Marcus Hartmann, Muenster (DE); Christine Sachse, Muenster (DE); Jenny Apelt, Muenster (DE); Ulrike Bockau, Muenster (DE)

(73) Assignee: Sanofi Pasteur S.A., Lyons (FR)

( * ) Notice: Subject to any disclaimer, the term of this patent is extended or adjusted under 35 U.S.C. 154(b) by 45 days.

(21) Appl. No.: 12/816,883

(22) Filed: Jun. 16, 2010

(65) Prior Publication Data

US 2011/0008835 A1 Jan. 13, 2011

(30) Foreign Application Priority Data

Jun. 17, 2009 (GB) .................................. 0910357.3

(51) Int. Cl.
*C12N 5/02* (2006.01)
*C12N 15/09* (2006.01)

(52) U.S. Cl. .................................. 435/257.1; 435/320.1

(58) Field of Classification Search ........................ None
See application file for complete search history.

(56) References Cited

U.S. PATENT DOCUMENTS

| | | | | |
|---|---|---|---|---|
| 4,752,473 | A | 6/1988 | Nayak | 424/88 |
| 5,858,368 | A | 1/1999 | Smith | 424/192.1 |
| 2003/0219869 | A1 | 11/2003 | Kiy | 435/6 |
| 2007/0286873 | A1 | 12/2007 | Williams | 435/6 |

FOREIGN PATENT DOCUMENTS

| | | |
|---|---|---|
| EP | 1151118 | 8/2000 |
| GB | 0910357.3 | 6/2009 |
| GB | 2471093 | 12/2010 |
| WO | WO 00/46381 | 8/2000 |
| WO | WO 03/006480 | 1/2003 |
| WO | WO 03/048348 | 6/2003 |
| WO | WO 03/078566 | 9/2003 |
| WO | WO 2007/006812 | 1/2007 |
| WO | WO 2007/022425 | 2/2007 |
| WO | WO 2010/146043 | 12/2010 |

OTHER PUBLICATIONS

Newby et al. J. Virol. 2007, vol. 81, (17), pp. 9469-9480.*
Kim et al. Dev. Genet, 1992, vol. 13 (2), pp. 97-102.*
Jabbar et al. Molecular and Cellular Biology, 1987, vol. 7, No. 4, pp. 1476-1485.*
Massion et al. American Journal of Respiratory Cell and Molecular , 1993, col. 9(4), pp. 361-370.*
Bos TJ, et al. NH2-terminal hydrophobic region of influenza virus neuraminidase provides the signal function in translocation, PNAS 81, pp. 2327-2331 (1984).
Cassidy-Hanley D, et al. Germline and somatic transformation of mating *Tetrahymena thermophila* by particle bombardment, Genetics 146, pp. 135-147 (1997).
Gaertig J, et al. Surface display of a parasite antigen in the ciliate *Tetrahymena thermophila*, Nat Biotechnol 17, pp. 462-465 (1999).
Jabbar MA & Nayak DP. Signal processing, glycosylation, and secretion of mutant hemagglutinins of a human influenza virus by *Saccharomyces cerevisiae*, Mol Cell Biol 7, pp. 1476-1485 (1987).
Jabbar MA, et al. Influenza viral (A/WSN/33) hemagglutinin is expressed and glycosylated in the yeast *Saccharomyces cerevisae*, PNAS 82, pp. 2019-2023 (1985).
Kim CS, et al. Bacteriophage λ DNA fragments replicate in the *Paramecium macronucleus*: absence of active copy number control, Dev Gen 13, pp. 97-102 (1992).
Kulakovsky P, et al. N-Linked glycosylation of a baculovirus-expressed recombinant glycoprotein in insect larvae and tissue culture cells, Glycobiology 8, pp. 741-745 (1998).
Kyte J & Doolittle RF. A simple method for displaying the hydropathic character of a protein, J Mol Biol 157, p. 105 (1982).
Massion PP, et al. *Parainfluenza* (Sendai) virus infects ciliated cells and secretory cells but not basal cells of rat tracheal epithelium, Am J Respir Cell Mol Biol 9, pp. 361-370 (1993).
Mochizuki K, et al. High efficiency transformation of Tetrahymena using a codon-optimized neomycin resistance gene, Gene 425, pp. 79-83 (2008).
Newby C, et al. The RNA binding domain of influenza A virus NS1 protein affects secretion of tumor necrosis factor alpha, interleukin-6, and interferon in primary murine tracheal epithelial cells, J Virol 81, pp. 9469-9480 (2007).
Reading P, et al. Involvement of the mannose receptor in infection of macrophages by influenza virus, J Virol 74, pp. 5190-5197 (2000).
Tomiya N, et al. Comparing N-glycan processing in mammalian cell lines to native and engineered lepidopteran insect cell lines, Glycoconj J 21, pp. 343-360 (2004).
Weide T, et al. Secretion of functional human enzymes by *Tetrahymena thermophila*, BMC Biotechnology 6, pp. 462-465 (2006).
Search Report issued Dec. 17, 2009 by the UK Intellectual Property Office for application No. GB 0910357.3 filed Jun. 17, 2009 (Applicant—Cilian AG // 1st Named Inventor—Hartmann) (2 pages).

* cited by examiner

*Primary Examiner* — Bao Li
(74) *Attorney, Agent, or Firm* — Ballard Spahr LLp

(57) ABSTRACT

The present invention relates to a system for the heterologous expression of a viral protein or a fragment thereof, said system comprising
a) a ciliate host cell,
b) at least one cDNA encoding for a viral protein, or a fragment thereof, and
c) a promoter operably linked to said cDNA.

7 Claims, 10 Drawing Sheets

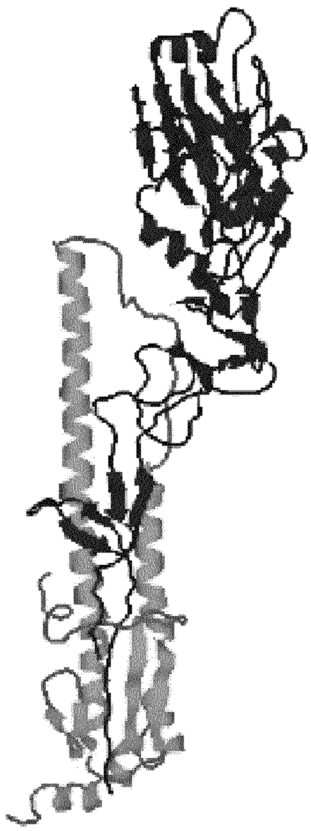
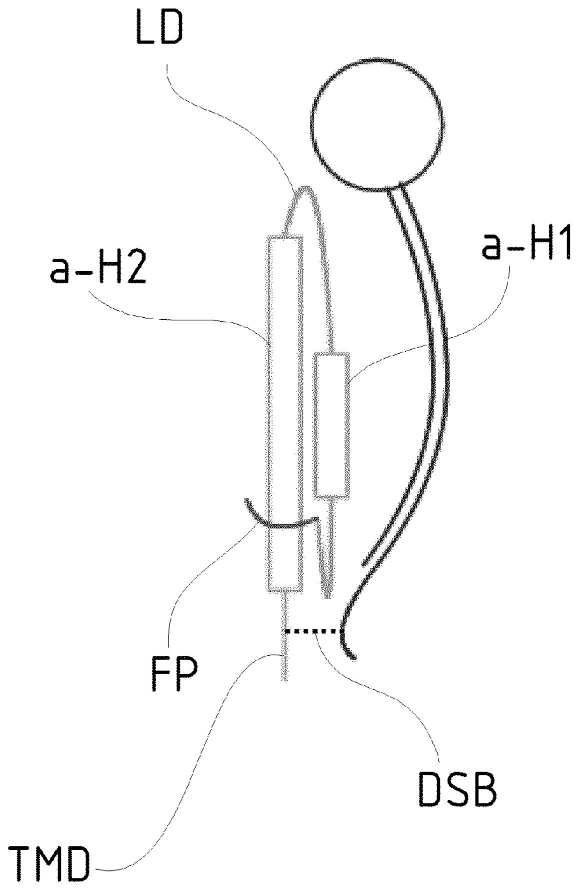
Fig. 3A
Fig. 3B

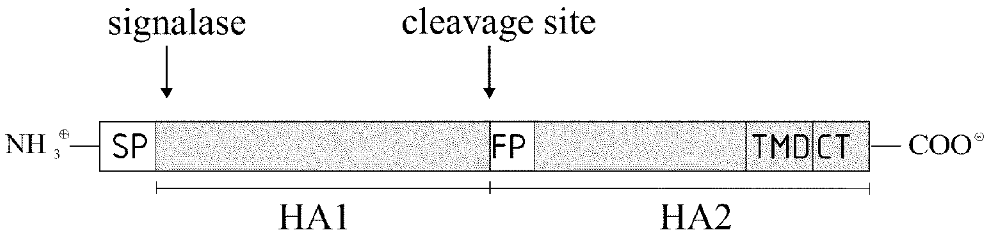

Fig. 4A

| Domain | AA | Symbol |
|---|---|---|
| Signal peptide | 1 - 17 | SP |
| HA1 extracellular domain | 18 - 343 | |
| HA2 Fusion peptide | 344 - 368 | FP |
| HA2 extracellular domain | 368 - 529 | |
| HA2 Transmembrane domain | 530 - 550 | TMD |
| HA2 Intracellular domain | 551 - 565 | CT |

10 20 30 40 50 60
MKAKLLVLLC TFTATYADTI CIGYHANNST DTVDTVLEKN VTVTHSVNLL EDSHNGKLCL 70 80 90 100 110 120
LKGIAPLQLG NCSVAGWILG NPECELLISK ESWSYIVETP NPENGTCYPG YFADYEELRE 130 140 150 160 170 180
QLSSVSSFER FEIFPKESSW PNHTVTGVSA SCSHNGKSSF YRNLLWLTGK NGLYPNLSKS 190 200 210 220 230 240
YVNNKEKEVL VLWGVHHPPN IGNQRALYHT ENAYVSVVSS HYSRRFTPEI AKRPKVRDQE 250 260 270 280 290 300
GRINYYWTLL EPGDTIIFEA NGNLIAPWYA FALSRGFGSG IITSNAPMDE CDAKCQTPQG 310 320 330 340 350 360
AINSSLPFQN VHPVTIGECP KYVRSAKLRM VTGLRNIPSI QSRGLFGAIA GFIEGGWTGM

370 380 390 400 410 420
VDGWYGYHHQ NEQGSGYAAD QKSTQNAING ITNKVNSVIE KMNTQFTAVG KEFNKLERRM 430 440 450 460 470 480
ENLNKKVDDG FLDIWTYNAE LLVLLENERT LDFHDSNVKN LYEKVKSQLK NNAKEIGNGC 490 500 510 520 530 540
FEFYHKCNNE CMESVKNGTY DYPKYSEESK LNREKIDGVK LESMGVYQIL AIYSTVASSL

550 560
VLLVSLGAIS FWMCSNGSLQ CRICI

Fig. 4B

*Tetrahymena thermophila* [gbinv]: 283 CDS's (145922 codons)

fields: [triplet] [frequency: per thousand] ([number])

| | | | |
|---|---|---|---|
| UUU 26.1( 3815) | UCU 24.4( 3557) | UAU 23.3( 3407) | UGU 9.7( 1412) |
| UUC 19.4( 2827) | UCC 6.5( 948) | UAC 14.5( 2110) | UGC 8.8( 1282) |
| UUA 29.8( 4346) | UCA 16.8( 2453) | UAA 36.8( 5366) | UGA 2.0( 286) |
| UUG 14.1( 2054) | UCG 1.5( 222) | UAG 11.0( 1606) | UGG 7.4( 1080) |
| CUU 20.3( 2955) | CCU 17.6( 2574) | CAU 8.7( 1267) | CGU 4.6( 677) |
| CUC 10.3( 1497) | CCC 4.6( 676) | CAC 6.4( 930) | CGC 0.9( 136) |
| CUA 7.4( 1078) | CCA 8.2( 1202) | CAA 19.8( 2894) | CGA 0.5( 73) |
| CUG 2.6( 378) | CCG 0.5( 68) | CAG 3.3( 477) | CGG 0.1( 8) |
| AUU 39.3( 5733) | ACU 27.2( 3968) | AAU 48.0( 7002) | AGU 13.5( 1963) |
| AUC 16.2( 2367) | ACC 7.8( 1140) | AAC 24.2( 3530) | AGC 9.2( 1344) |
| AUA 19.1( 2783) | ACA 14.8( 2153) | AAA 58.7( 8562) | AGA 26.6( 3887) |
| AUG 19.3( 2811) | ACG 0.8( 111) | AAG 34.3( 5001) | AGG 2.8( 412) |
| GUU 25.8( 3763) | GCU 30.3( 4428) | GAU 42.5( 6208) | GGU 24.5( 3576) |
| GUC 10.1( 1469) | GCC 7.5( 1098) | GAC 12.4( 1815) | GGC 4.3( 629) |
| GUA 11.6( 1693) | GCA 11.8( 1726) | GAA 58.2( 8499) | GGA 15.1( 2205) |
| GUG 3.1( 451) | GCG 0.6( 88) | GAG 11.2( 1630) | GGG 1.5( 216) |

Coding GC 32.53% 1st letter GC 38.64% 2nd letter GC 31.25% 3rd letter GC 27.69%

*Homo sapiens* [gbpri]: 93487 CDS's (40662582 codons)

fields: [triplet] [frequency: per thousand] ([number])

| | | | |
|---|---|---|---|
| UUU 17.6(714298) | UCU 15.2(618711) | UAU 12.2(495699) | UGU 10.6(430311) |
| UUC 20.3(824692) | UCC 17.7(718892) | UAC 15.3(622407) | UGC 12.6(513028) |
| UUA 7.7(311881) | UCA 12.2(496448) | UAA 1.0( 40285) | UGA 1.6( 63237) |
| UUG 12.9(525688) | UCG 4.4(179419) | UAG 0.8( 32109) | UGG 13.2(535595) |
| CUU 13.2(536515) | CCU 17.5(713233) | CAU 10.9(441711) | CGU 4.5(184609) |
| CUC 19.6(796638) | CCC 19.8(804620) | CAC 15.1(613713) | CGC 10.4(423516) |
| CUA 7.2(290751) | CCA 16.9(688038) | CAA 12.3(501911) | CGA 6.2(250760) |
| CUG 39.6(1611801) | CCG 6.9(281570) | CAG 34.2(1391973) | CGG 11.4(464485) |
| AUU 16.0(650473) | ACU 13.1(533609) | AAU 17.0(689701) | AGU 12.1(493429) |
| AUC 20.8(846466) | ACC 18.9(768147) | AAC 19.1(776603) | AGC 19.5(791383) |
| AUA 7.5(304565) | ACA 15.1(614523) | AAA 24.4(993621) | AGA 12.2(494682) |
| AUG 22.0(896005) | ACG 6.1(246105) | AAG 31.9(1295568) | AGG 12.0(486463) |
| GUU 11.0(448607) | GCU 18.4(750096) | GAU 21.8(885429) | GGU 10.8(437126) |
| GUC 14.5(588138) | GCC 27.7(1127679) | GAC 25.1(1020595) | GGC 22.2(903565) |
| GUA 7.1(287712) | GCA 15.8(643471) | GAA 29.0(1177632) | GGA 16.5(669873) |
| GUG 28.1(1143534) | GCG 7.4(299495) | GAG 39.6(1609975) | GGG 16.5(669768) |

Coding GC 52.27% 1st letter GC 55.72% 2nd letter GC 42.54% 3rd letter GC 58.55%

Fig. 5

| 1LC | 3LC | amino acid | Codons | | | | | |
|---|---|---|---|---|---|---|---|---|
| A | Ala | Alanine | GCU | GCA | GCC | GCG | | |
| C | Cys | Cysteine | UGU | UGC | | | | |
| D | Asp | Aspartic acid | GAU | GAC | | | | |
| E | Glu | Glutamic acid | GAA | GAG | | | | |
| F | Phe | Phenylalanine | UUU | UUC | | | | |
| G | Gly | Glycine | GGU | GGA | GGC | GGG | | |
| H | His | Histidine | CAU | CAC | | | | |
| I | Ile | Isoleucine | AUU | AUA | AUC | | | |
| K | Lys | Lysine | AAA | AAG | | | | |
| L | Leu | Leucine | UUA | CUU | UUG | CUC | CUA | CUG |
| M | Met | Methionine /START | AUG | | | | | |
| N | Asn | Asparagine | AAU | AAC | | | | |
| P | Pro | Proline | CCU | CCA | CCC | CCG | | |
| Q | Gln | Glutamine | CAA | CAG | **UAA** | **UAG** | | |
| R | Arg | Arginine | AGA | CGU | AGG | CGC | CGA | CGG |
| S | Ser | Serine | UCU | UCA | AGU | AGC | UCC | UCG |
| T | Thr | Threonine | ACU | ACA | ACC | ACG | | |
| V | Val | Valine | GUU | GUA | GUC | GUG | | |
| W | Trp | Tryptophan | UGG | | | | | |
| Y | Tyr | Tyrosine | UAU | UAC | | | | |
| | | STOP | UGA | ~~UAA~~ | ~~UAG~~ | | | |

Fig. 6

SEQUENCE LISTING

```
<160> NUMBER OF SEQ ID NOS: 15

<210> SEQ ID NO 1
<211> LENGTH: 1697
<212> TYPE: DNA
<213> ORGANISM: Influenza virus

<400> SEQUENCE: 1

atgaaagcaa aactactggt cctgttatgt acatttacag ctacatatgc agacacaata     60

tgtataggct accatgccaa caactcaacc gacactgttg acacagtact tgagaagaat    120

gtgacagtga cacactctgt caacctactt gaggacagtc acaatggaaa actatgtcta    180

ctaaaaggaa tagccccact acaattgggt aattgcagcg ttgccggatg gatcttagga    240

aacccagaat gcgaattact gatttccaag gaatcatggt cctacattgt agaaacacca    300

aatcctgaga atggaacatg ttacccaggg tatttcgccg actatgagga actgagggag    360

caattgagtt cagtatcttc atttgagaga ttcgaaatat tccccaaaga aagctcatgg    420

cccaaccaca ccgtaaccgg agtatcagca tcatgctccc ataatgggaa aagcagtttt    480

tacagaaatt tgctatggct gacggggaag aatggtttgt acccaaacct gagcaagtcc    540

tatgtaaaca acaaagagaa agaagtcctt gtactatggg gtgttcatca cccgcctaac    600

atagggaacc aaagggccct ctatcataca gaaaatgctt atgtctctgt agtgtcttca    660

cattatagca gaagattcac cccagaaata gccaaaagac ccaaagtaag agatcaggaa    720

ggaagaatca actactactg gactctgctg gaacctgggg atacaataat atttgaggca    780

aatggaaatc taatagcgcc atggtatgct tttgcactga gtagaggctt tggatcagga    840
```

-continued

```
atcatcacct caaatgcacc aatggatgaa tgtgatgcga agtgtcaaac acctcaggga    900

gctataaaca gcagtcttcc tttccagaat gtacacccag tcacaatagg agagtgtcca    960

aagtatgtca ggagtgcaaa attaaggatg gttacaggac taaggaacat cccatccatt   1020

caatccagag gtttgtttgg agccattgcc ggtttcattg aaggggggtg gactggaatg   1080

gtagatgggt ggtatggtta tcatcatcag aatgagcaag gatctggcta tgctgcagat   1140

caaaaaagta cacaaaatgc cattaacggg attacaaaca aggtgaattc tgtaattgag   1200

aaaatgaaca ctcaattcac agctgtgggc aaagaattca acaaattgga aagaaggatg   1260

gaaaacttaa ataaaaaagt tgatgatggg tttctagaca tttggacaat aatgcagaat   1320

tgttggttct actggaaaat gaaaggactt tggatttcca tgactccaat gtgaagaatc   1380

tgtatgagaa agtaaaaagc caattaaaga ataatgccaa agaaatagga aacgggtgtt   1440

ttgaattcta tcacaagtgt aacaatgaat gcatggagag tgtgaaaaat ggaacttatg   1500

actatccaaa atattccgaa gaatcaaagt taaacaggga gaaaattgat ggagtgaaat   1560

tggaatcaat gggagtctat cagattctgg cgatctactc aactgtcgcc agttccctgg   1620

ttcttttggt ctccctgggg gcaatcagct tctggatgtg ttccaatggg tctttgcagt   1680

gtagaatatg catctga                                                  1697
```

<210> SEQ ID NO 2
<211> LENGTH: 1698
<212> TYPE: DNA
<213> ORGANISM: Influenza virus

<400> SEQUENCE: 2

```
atgaaagcta agttattagt tttactttgt actttcactg ctacttatgc tgatactatt     60

tgtattggtt atcacgctaa taattctact gatactgttg atactgtttt agaaaaaaat    120

gttactgtta ctcactctgt taatctttta gaagattctc acaatggtaa attatgttta    180

cttaaaggta ttgctccttt ataacttggt aattgttctg ttgctggttg gattcttggt    240

aatcctgaat gtgaattact tatttctaaa gaatcttggt cttatattgt tgaaactcct    300

aatcctgaaa atggtacttg ttatcctggt tatttcgctg attatgaaga attaagagaa    360

taactttctt ctgtttcttc atttgaaaga ttcgaaattt tccctaaaga atcttcttgg    420

cctaatcaca ctgttactgg tgtttctgct tcttgttctc ataatggtaa atcttcattc    480

tatagaaatc ttttatggtt aactggtaaa aatggtttat atcctaatct ttctaaatct    540

tatgttaata ataaggaaaa agaagtttta gttctttggg gtgttcacca ccctcctaat    600

attggtaatt aaagagcttt atatcacact gaaaatgctt atgtttctgt tgtttcttct    660

cactattcta gaagattcac tcctgaaatt gctaaaagac ctaaagttag agattaagaa    720

ggtagaatta actattattg gactttatta gaacctggtg atactattat tttcgaagct    780

aatggtaatc ttattgctcc ttggtacgct ttcgctttat ctagaggttt cggttctggt    840

attattactt ctaatgctcc tatggatgaa tgtgatgcta aatgttaaac tccttaaggt    900

gctattaatt cttctttacc tttctaaaac gttcaccctg ttactattgg tgaatgtcct    960

aaatatgtta gatcagctaa attaagaatg gttactggtt taagaaatat tccttctatc   1020

taatctagag gacttttcgg tgctattgct ggtttcattg agggaggatg gacaggtatg   1080

gttgatggtt ggtacggtta tcaccaccaa aatgaataag gttctggtta tgctgctgat   1140

taaaagtcta ctcaaaacgc tattaatggt attactaaca aagttaattc tgttattgaa   1200

aaaatgaata cttaattcac tgctgttggt aaagaattca ataagttaga aagaagaatg   1260
```

-continued

```
gaaaatctta ataagaaagt tgatgatggt ttcttagata tttggactta taatgctgaa   1320

ttattagttc ttttagaaaa tgaaagaact ttagatttcc acgattctaa tgttaaaaat   1380

ctttatgaaa aagttaaatc ttaacttaag aataatgcta aagaaattgg taatggttgt   1440

ttcgaattct atcacaaatg taataatgaa tgtatggaat ctgttaagaa tggtacttat   1500

gattatccta aatattctga agaatctaag ttaaatagag aaaaaattga tggtgttaaa   1560

ttagaatcta tgggagttta ctaaattctt gctatctatt ctactgttgc ttcttcttta   1620

gttttattag tttctttagg tgctatttct ttctggatgt gttctaatgg ttctttataa   1680

tgtagaattt gtatttga                                                  1698
```

<210> SEQ ID NO 3
<211> LENGTH: 550
<212> TYPE: PRT
<213> ORGANISM: Influenza virus

<400> SEQUENCE: 3

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Thr His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300
```

```
Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser
545                 550
```

<210> SEQ ID NO 4
<211> LENGTH: 1604
<212> TYPE: DNA
<213> ORGANISM: Influenza virus

<400> SEQUENCE: 4

```
ggcgcgccat ggatatcaaa gctaagttat tagttttact ttgtactttc actgctactt     60

atgctgatac tatttgtatt ggttatcacg ctaataattc tactgatact gttgatactg    120

ttttagaaaa aaatgttact gttactcact ctgttaatct tttagaagat tctcacaatg    180

gtaaattatg tttacttaaa ggtattgctc ctttataact tggtaattgt tctgttgctg    240

gttggattct tggtaatcct gaatgtgaat tacttatttc taaagaatct tggtcttata    300

ttgttgaaac tcctaatcct gaaaatggta cttgttatcc tggttatttc gctgattatg    360

aagaattaag agaataactt tcttctgttt cttcatttga aagattcgaa attttcccta    420

aagaatcttc ttggcctaat cacactgtta ctggtgtttc tgcttcttgt tctcataatg    480

gtaaatcttc attctataga aatcttttat ggttaactgg taaaaatggt ttatatccta    540

atctttctaa atcttatgtt aataataagg aaaaagaagt tttagttctt tggggtgttc    600

accaccctcc taatattggt aattaaagag ctttatatca cactgaaaat gcttatgttt    660

ctgttgtttc ttctcactat tctagaagat tcactcctga aattgctaaa agacctaaag    720
```

```
ttagagatta agaaggtaga attaactatt attggacttt attagaacct ggtgatacta    780

ttattttcga agctaatggt aatcttattg ctccttggta cgctttcgct ttatctagag    840

gtttcggttc tggtattatt acttctaatg ctcctatgga tgaatgtgat gctaaatgtt    900

aaactcctta aggtgctatt aattcttctt tacctttcta aaacgttcac cctgttacta    960

ttggtgaatg tcctaaatat gttagatcag ctaaattaag aatggttact ggtttaagaa   1020

atattccttc tatctaatct agaggacttt tcggtgctat tgctggtttc attgagggag   1080

gatggacagg tatggttgat ggttggtacg gttatcacca ccaaaatgaa taaggttctg   1140

gttatgctgc tgattaaaag tctactcaaa acgctattaa tggtattact aacaaagtta   1200

attctgttat tgaaaaaatg aatacttaat tcactgctgt tggtaaagaa ttcaataagt   1260

tagaaagaag aatggaaaat cttaataaga aagttgatga tggtttctta gatatttgga   1320

cttataatgc tgaattatta gttcttttag aaaatgaaag aactttagat ttccacgatt   1380

ctaatgttaa aaatctttat gaaaaagtta aatcttaact taagaataat gctaaagaaa   1440

ttggtaatgg ttgtttcgaa ttctatcaca aatgtaataa tgaatgtatg gaatctgtta   1500

agaatggtac ttatgattat cctaaatatt ctgaagaatc taagttaaat agagaaaaaa   1560

ttgatggtgt taaattagaa tctatgggag tttactaaat ttga                    1604
```

```
<210> SEQ ID NO 5
<211> LENGTH: 538
<212> TYPE: PRT
<213> ORGANISM: Influenza virus

<400> SEQUENCE: 5

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Thr His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220
```

```
Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser
    530                 535
```

<210> SEQ ID NO 6
<211> LENGTH: 1032
<212> TYPE: DNA
<213> ORGANISM: Influenza virus

<400> SEQUENCE: 6

```
atcaaagcta agttattagt tttactttgt actttcactg ctacttatgc tgatactatt      60

tgtattggtt atcacgctaa taattctact gatactgttg atactgtttt agaaaaaaat     120

gttactgtta ctcactctgt taatctttta gaagattctc acaatggtaa attatgttta     180

cttaaaggta ttgctccttt ataacttggt aattgttctg ttgctggttg gattcttggt     240

aatcctgaat gtgaattact tatttctaaa gaatcttggt cttatattgt tgaaactcct     300

aatcctgaaa atggtacttg ttatcctggt tatttcgctg attatgaaga attaagagaa     360
```

```
taactttctt ctgtttcttc atttgaaaga ttcgaaattt tccctaaaga atcttcttgg    420

cctaatcaca ctgttactgg tgtttctgct tcttgttctc ataatggtaa atcttcattc    480

tatagaaatc ttttatggtt aactggtaaa aatggtttat atcctaatct ttctaaatct    540

tatgttaata ataaggaaaa agaagtttta gttctttggg gtgttcacca ccctcctaat    600

attggtaatt aaagagcttt atatcacact gaaaatgctt atgtttctgt tgtttcttct    660

cactattcta gaagattcac tcctgaaatt gctaaaagac ctaaagttag agattaagaa    720

ggtagaatta actattattg gactttatta gaacctggtg atactattat tttcgaagct    780

aatggtaatc ttattgctcc ttggtacgct ttcgctttat ctagaggttt cggttctggt    840

attattactt ctaatgctcc tatggatgaa tgtgatgcta aatgttaaac tccttaaggt    900

gctattaatt cttctttacc tttctaaaac gttcaccctg ttactattgg tgaatgtcct    960

aaatatgtta gatcagctaa attaagaatg gttactggtt taagaaatat tccttctatc   1020

taatctagat ga                                                        1032


<210> SEQ ID NO 7
<211> LENGTH: 343
<212> TYPE: PRT
<213> ORGANISM: Influenza virus

<400> SEQUENCE: 7

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Thr His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255
```

```
Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg
            340


<210> SEQ ID NO 8
<211> LENGTH: 328
<212> TYPE: DNA
<213> ORGANISM: Tetrahymena thermophila

<400> SEQUENCE: 8

atgaacaaga ctctcatctt agctttagtt ggtgttttgg ctttaactgc caccaccttg      60

gttgctttcc acaaccactc tcacaacatc agagttgact aagaccccgc cactctcttc     120

aagcaattca agcaaactta caataagaag tatgctgatc ctactttcga aacctacaga     180

ttcggtgtct tcacccaaaa cttagaaatc gtcaagactg actctacttt cggtgtcacc     240

taattcatgg acttaactcc tgctgaattc gctcaacaat tcctcacttt acacgaaaag     300

gttaacagca ccgaagttta cagagctc                                        328


<210> SEQ ID NO 9
<211> LENGTH: 113
<212> TYPE: PRT
<213> ORGANISM: Tetrahymena thermophila

<400> SEQUENCE: 9

Met Asn Lys Thr Leu Ile Leu Ala Leu Val Val Val Leu Ala Leu Thr
1               5                   10                  15

Ala Thr Thr Leu Val Ala Phe His Asn His Ser His Asn Ile Arg Val
            20                  25                  30

Asp Gln Asp Pro Ala Thr Leu Phe Lys Gln Phe Lys Gln Thr Tyr Asn
        35                  40                  45

Lys Lys Tyr Ala Asp Ala Thr Phe Glu Thr Tyr Arg Phe Gly Val Phe
    50                  55                  60

Thr Gln Asn Leu Glu Ile Val Lys Thr Asp Ser Thr Phe Gly Val Thr
65                  70                  75                  80

Gln Phe Met Asp Leu Thr Pro Ala Glu Phe Ala Gln Gln Phe Leu Thr
                85                  90                  95

Leu His Glu Lys Val Asn Ser Thr Glu Val Tyr Arg Ala Gln Gly Glu
            100                 105                 110

Ala


<210> SEQ ID NO 10
<211> LENGTH: 65
<212> TYPE: DNA
<213> ORGANISM: Influenza virus

<400> SEQUENCE: 10

ggcgcgccat ggatatcaaa gctaagttat tagttttact ttgtactttc actgctactt      60
```

-continued

```
atgct                                                              65


<210> SEQ ID NO 11
<211> LENGTH: 17
<212> TYPE: PRT
<213> ORGANISM: Influenza virus

<400> SEQUENCE: 11

Met Lys Ala Lys Leu Leu Val Leu Leu Cys Thr Phe Thr Ala Thr Tyr
1               5                   10                  15

Ala


<210> SEQ ID NO 12
<211> LENGTH: 980
<212> TYPE: DNA
<213> ORGANISM: Tetrahymena thermophila

<400> SEQUENCE: 12

agcatgcttt ttcatgtact attcctaact atagcttaat gctttataca tcaaagtatg     60

aagaagacag gttttaaaaa accaaaaaat atgtttttta tttgaaaagt attatatagg    120

aataataaat gctgcataaa tactctaagt agttgataaa aaatctattt atgcaaagaa    180

aaatttagaa aaatttagaa aaacaaagaa aataattgtt attataaagc attttgttta    240

ctaagcaaaa gatataaaat ttgagataga aatatacata caagattaac gttttgtttg    300

tgctttgaaa attgaaatat ttaattatta aatctgctaa ctttttttaga tatttatttg    360

ctttatttta ttttttaaat ttttgcaaag tggagaaaaa tgaaacaatc aatctttttt    420

ttataaataa tataaatggt attaagccta atttttattg ctggagagtg ttattcaaat    480

atattgctga atgtggctag atggaattcg ctttggaagg aaagtgttta taaaataagt    540

gatgtattat agcacattgc taattattat aaagaatgta ttggatattt aaaaattaga    600

aaataaaatt tagctgaaaa gtaagaaagc aagcaaagat atatatatat atatggagat    660

gataaaaaga taaattcgaa aaaagaaaat ttctaaagtg aaaagaatta tggatttgat    720

taaataaaaa tatttttaga atgggctgat taaagaggga tcttcgagaa tgaaatgatt    780

tagaaaaaaa gaaagaaaga ttataacatc tacaaagagt tgaagattct agaagaggag    840

gaataattag ctatcagtct tattaaaaga tatcgcaaaa caagaaatat ttttgaaatt    900

aattaaaaaa tttaaaaaac aaaagataaa aattttgcac aaaaaagcaa ttaattaaaa    960

aaaaagatat atcataagaa                                                980


<210> SEQ ID NO 13
<211> LENGTH: 998
<212> TYPE: DNA
<213> ORGANISM: Tetrahymena thermophila

<400> SEQUENCE: 13

tcgaggataa gtaatatatt tagtgcacaa tgtttgaatg ttttttttgat aaatttgtaa     60

attaaatcta tttaagtcag tagaatttta gatattttca tagatttttt aataagtaga    120

caatttattt ctaaaaaata tttaaaaata aaaaataata agggttttga ataactcctt    180

taatttaaat acacattttt aaattttttt tagctcttta aatattcata aaaataaaaa    240

ataactaact aaaaataaat aaaaagataa taatgattaa aggtataata ctgaataaga    300

aaaaacataa tagagtactt atttttttata tcactatttt taatatcttg aaagcaaaac    360

tttttatat atcttaaaat atattgtatc gtttattcaa ttattttctt taaatttcaa    420

atatattgat aaaaaagatg acatgttttt taaagaaaac atgaaatata aaatagataa    480
```

-continued

```
atatcaatta ttttatttat taaatatata agctgctcaa aacatagctc attcatcaat    540
tataatatgt gaatcattaa ttttcaaaat attactcatt atttaggcta tcatttattt    600
tttattttca attatccgtt tctattatat tttaatatta agttgtgatt cttgaatttt    660
gtgtcatgaa ttatttgtaa atctttttat ttctgataaa aaatataaat tgattgactc    720
atgatttaaa tcatgagtca acctaactaa ttttcaaaat tcttctattc taaaatatag    780
atgtgattct tgaatctctc ttgaatataa agtaattttt tatatttctg atataattct    840
tagctacgtg attcacgatt tatgcaatga tccatataaa ataatgtaaa tagtgtatat    900
atatatattc gtctttttta ttctttatat aatttaaaaa aattaaaaaa atttaataaa    960
gctctaataa aataaataat aatactaaac ttaaaata                            998
```

<210> SEQ ID NO 14
<211> LENGTH: 1722
<212> TYPE: DNA
<213> ORGANISM: Influenza virus

<400> SEQUENCE: 14

```
atgaaggcaa taattgtact actcatggta gtaacatcca atgcagatcg aatctgcact     60
ggaataacat cttcaaactc acctcatgtg gtcaaaacag ccactcaagg ggaggtcaat    120
gtgactggtg tgataccact aacaacaaca ccaacaaaat cttattttgc aaatctcaaa    180
ggaacaagga ccagagggaa actatgccca gactgtctca actgcacaga tctggatgtg    240
gctttgggca gaccaatgtg tgtggggacc acaccttcgg cgaaagcttc aatactccac    300
gaagtcaaac ctgttacatc cgggtgcttt cctataatgc acgacagaac aaaaatcagg    360
caactaccca atcttctcag aggatatgaa aatatcaggc tatcaaccca aaacgtcatc    420
gatgcggaaa aggcaccagg aggaccctac agacttggaa cctcaggatc ttgccctaac    480
gctaccagta agagcggatt tttcgcaaca atggcttggg ctgtcccaaa ggacaacaac    540
aaaaatgcaa cgaacccact aacagtagaa gtaccataca tttgtacaga aggggaagac    600
caaatcactg tttgggggtt ccattcagat gacaaaaccc aaatgaagaa cctctatgga    660
gactcaaatc ctcaaaagtt cacctcatct gctaatggag taaccacaca ctatgtttct    720
cagattggca gcttcccaga tcaaacagaa gacggaggac taccacaaag cggcaggatt    780
gttgttgatt acatgatgca aaaacctggg aaaacaggaa caattgtcta ccaaagaggt    840
gttttgttgc ctcaaaaggt gtggtgcgcg agtggcagga gcaaagtaat aaaagggtcc    900
ttgcctttaa ttggtgaagc agattgcctt catgaaaaat acggtggatt aaacaaaagc    960
aagccttact acacaggaga acatgcaaaa gccataggaa attgcccaat atgggtgaaa   1020
acacctttga agcttgccaa tggaaccaaa tatagacctc ctgcaaaact attaaaggaa   1080
aggggtttct tcggagctat tgctggtttc ctagaaggag gatgggaagg aatgattgca   1140
ggctggcacg gatacacatc tcacggagca catggagtgg cagtggcggc ggaccttaag   1200
agtacgcaag aagctataaa caagataaca aaaaatctca attctttgag tgagctagaa   1260
gtaaagaatc ttcaaagact aagtggtgcc atggatgaac tccacaacga aatactcgag   1320
ctggatgaga aagtggatga tctcagagct gacactataa gctcgcaaat agaacttgca   1380
gtcttgcttt ccaacgaagg aataataaac agtgaagatg agcatctatt ggcacttgag   1440
agaaaactaa agaaaatgct gggtccctct gctgtagaga taggaaatgg atgcttcgaa   1500
accaaacaca agtgcaacca gacctgctta gacaggatag ctgctggcac ctttaatgca   1560
ggagaatttt ctctccccac ttttgattca ctgaacatta ctgctgcatc tttaaatgat   1620
```

gatggattgg ataaccatac tatactgctc tattactcaa ctgctgcttc tagtttggct 1680
gtaacattga tgctagctat ttttattgtt tatatggtct cc 1722

<210> SEQ ID NO 15
<211> LENGTH: 574
<212> TYPE: PRT
<213> ORGANISM: Influenza virus

<400> SEQUENCE: 15

Met Lys Ala Ile Ile Val Leu Leu Met Val Val Thr Ser Asn Ala Asp
1 5 10 15

Arg Ile Cys Thr Gly Ile Thr Ser Ser Asn Ser Pro His Val Val Lys
20 25 30

Thr Ala Thr Gln Gly Glu Val Asn Val Thr Gly Val Ile Pro Leu Thr
35 40 45

Thr Thr Pro Thr Lys Ser Tyr Phe Ala Asn Leu Lys Gly Thr Arg Thr
50 55 60

Arg Gly Lys Leu Cys Pro Asp Cys Leu Asn Cys Thr Asp Leu Asp Val
65 70 75 80

Ala Leu Gly Arg Pro Met Cys Val Gly Thr Thr Pro Ser Ala Lys Ala
85 90 95

Ser Ile Leu His Glu Val Lys Pro Val Thr Ser Gly Cys Phe Pro Ile
100 105 110

Met His Asp Arg Thr Lys Ile Arg Gln Leu Pro Asn Leu Leu Arg Gly
115 120 125

Tyr Glu Asn Ile Arg Leu Ser Thr Gln Asn Val Ile Asp Ala Glu Lys
130 135 140

Ala Pro Gly Gly Pro Tyr Arg Leu Gly Thr Ser Gly Ser Cys Pro Asn
145 150 155 160

Ala Thr Ser Lys Ser Gly Phe Phe Ala Thr Met Ala Trp Ala Val Pro
165 170 175

Lys Asp Asn Asn Lys Asn Ala Thr Asn Pro Leu Thr Val Glu Val Pro
180 185 190

Tyr Ile Cys Thr Glu Gly Glu Asp Gln Ile Thr Val Trp Gly Phe His
195 200 205

Ser Asp Asp Lys Thr Gln Met Lys Asn Leu Tyr Gly Asp Ser Asn Pro
210 215 220

Gln Lys Phe Thr Ser Ser Ala Asn Gly Val Thr Thr His Tyr Val Ser
225 230 235 240

Gln Ile Gly Ser Phe Pro Asp Gln Thr Glu Asp Gly Gly Leu Pro Gln
245 250 255

Ser Gly Arg Ile Val Val Asp Tyr Met Met Gln Lys Pro Gly Lys Thr
260 265 270

Gly Thr Ile Val Tyr Gln Arg Gly Val Leu Leu Pro Gln Lys Val Trp
275 280 285

Cys Ala Ser Gly Arg Ser Lys Val Ile Lys Gly Ser Leu Pro Leu Ile
290 295 300

Gly Glu Ala Asp Cys Leu His Glu Lys Tyr Gly Gly Leu Asn Lys Ser
305 310 315 320

Lys Pro Tyr Tyr Thr Gly Glu His Ala Lys Ala Ile Gly Asn Cys Pro
325 330 335

Ile Trp Val Lys Thr Pro Leu Lys Leu Ala Asn Gly Thr Lys Tyr Arg
340 345 350

Pro Pro Ala Lys Leu Leu Lys Glu Arg Gly Phe Phe Gly Ala Ile Ala

-continued

```
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser
                565                 570
```

SYSTEM FOR THE HETEROLOGOUS EXPRESSION OF A VIRAL PROTEIN IN A CILIATE HOST CELL

CROSS REFERENCE TO RELATED APPLICATIONS

This application claims benefit of Great Britain Patent Application No. 0910357.3, filed Jun. 17, 2009, which application is hereby incorporated by this reference in its entirety.

SEQUENCE LISTING

In the appendix, a full sequence listing is added, which refers to the following sequences (NA: nucleic acid; AA; amino acid).

BACKGROUND OF THE INVENTION

The present invention relates to a system for the heterologous expression of a viral protein in a ciliate host cell.

As many viruses play a considerable role as human or animal pathogens, attention has been drawn to the use of viral proteins as vaccines against viral pathogens. Viruses (especially RNA viruses) are highly variable and many viral infections are due to viruses with multiple serotypes (e.g. Influenza virus, FMD virus). As a consequence, many of the existing viral vaccines are often unable to cope with the prevailing strains in the field and new ones have to be generated from the field strains with new outbreaks.

Despite the fact that, grace to modern biotechnology techniques, methods are available which allow for the heterologous expression of almost every conceivable protein, the expression of viral proteins is not such a common thing today, as viral proteins are, in most cases, structural proteins, i.e., neither enzymes nor protein hormones nor antibodies, and thus not that interesting for pharmaceutical or industrial purposes.

However, as many viruses play a considerable role as human or animal pathogens, attention has been drawn to the use of viral proteins as vaccines against viral pathogens.

Today, the standard procedure of producing vaccines against viral pathogens is to cultivate the respective virus in a given system, collect and inactivate virus particles thus obtained, and manufacture a pharmaceutical composition comprising said inactivated particles as a vaccine.

Said principle is for example practised in the production of influenza vaccine, which is being produced in fertilized chicken eggs. Eleven days after fertilization, the influenza virus strains are injected into the albumin of individual eggs and then infects the lungs of the developing embryo. After several days of incubation, the viruses are harvested and purified, chemically inactivated and used to produce a vaccine. On average, about one and two eggs are needed to produce one dose of vaccine. The entire production process lasts at least six months.

This way of vaccine production is well established and cost-effective, but has disadvantages as the procurement of many million eggs, the long timeline the tedious handling of the eggs and the limited flexibility in case of rapidly increasing demand or sudden appearance of new virus strains. Furthermore, fertilized chicken eggs can not be used to produce vaccines against a number of pathogenic virus, amongst them avian Influenza A virus (H5N1).

Anyway, fertilized chicken eggs can at least principally be used for the production of all viruses which are compatible with chicken embryoes as a host, or for the production of vaccines comprising elements of the former.

An alternative way of producing viruses, or vaccines comprising elements of the former is based on cell or tissue cultures. In one approach, the virus is injected into mammalian kidney cells. After propagation of the virus, the cells are lysed and then virus particles are harvested, purified and inactivated. However, these systems require the use of complex growing media, and their handling is laborious and time consuming. Furthermore, the said infection approach is difficult to carry out and not fully reproducible.

In another approach disclosed in WO03048348 a method for producing inactivated virus vaccines on the human cell line PER.C6® is disclosed. Because of the presence of the Sia2-6Gal and the Sia2-3Gal containing receptors on its surface this cell line is highly infectable with different viruses like Influenza virus, parainfluenza virus, adeno-associated virus or poliomavirus types. That might cause safety problems regarding the production process.

On the one hand mammalian cell culture based systems can, in contrast to the above egg based systems, be rapidly expanded and scaled up in times of emergency. On the other hand up-front costs for operational readiness of such production facilities (with its huge bioreactors) are much higher than the costs for egg-based systems, and the yield may be slightly slower. Again, these systems require the use of complex growing media, and their handling is laborious and time consuming.

Therefore, the development of alternative methods for the production of viral proteins which can be used as vaccines has high priority.

One approach is the production of those proteins using recombinant DNA techniques. One obvious advantage is a greatly improved safety of the vaccine, because of the opportunity to purify recombinant expressed viral protein in contrast to the vaccine production using eggs. Furthermore, the flexibility to adapt to different seasonal virus subtypes is highly increased.

However, as viral proteins are, in most cases structural proteins, the production for pharmaceutical and industrial purposes is complex and laborious. In the beginning it was attempted to express polypeptides corresponding to viral proteins like hemagglutinin in *Escherichia coli*. It is however noteworthy that heterologous expression of proteins which are to be used as vaccines in prokaryotes does not make sense, as the latter do not have a posttranslational modification apparatus. Therefore, proteins expressed in prokaryotes like *Escherichia coli* lack posttranslational modifications, like glycosylation pattern, which appears to affect the stability and contribute to a large extent to the immunogenic potential of an antigen. (Nayak et al. 1984).

Expression of viral proteins in the eukaryotic organism *Saccharomyces cerevisiae* (U.S. Pat. No. 4,752,473 for hemagglutinin) caused problems by the hyper-glycosylation of recombinant protein with the extensive addition of high molecular weight outer chain mannans (Jabbar and Nayak 1987, Jabbar et al. 1985) and had not proved satisfactory.

U.S. Pat. No. 5,858,368 discloses a method to express Influenza A virus hemagglutinin (HA) in recombinant baculovirus-infected insect cell lines. The proteins are chromatographically purified after being extracted from the peripheral membranes of the infected cells with a non-denaturing, nonionic detergent. The purification process is however rather time-consuming. Furthermore, it is questionable whether or not, due to their glycosylation pattern, proteins produced in a baculovirus/insect cell expression system are suitable for therapeutical use in mammals (Kulakosky et al. 1998). There are furthermore hints that certain residues in N-glycans of proteins expressed in insect cells represent potential allergenic epitopes (Tomiya et al. 2004).

BRIEF SUMMARY OF INVENTION

The object of the present invention is to provide a method and/or an embodiment which overcomes the disadvantages as set forth above. Such object is solved by embodiments set forth in the independent claims.

BRIEF DESCRIPTION OF DRAWINGS

It is obvious that, while prokaryotes have no N-glycosylation at all, ciliates feature N-glycosylation patterns which are rich in mannose, and thus enhance the immunogenic potential of a protein (see text).

FIG. 3A shows a hemagglutinin with its subunits HA1 (black) und HA2 (grey). Alpha helices and beta sheets are indicated.

FIG. 3B shows a schematic drawing of hemagglutinin with subunits HA1(black) und HA2. The fusion peptide (FP, see above) is shown as well as the transmembrane domain (TMD) which anchors the protein in the virus envelope membrane. HA1 and HA2 are linked by a disulfide bridge (DSB). The section of HA2 which connects the two $\alpha$-helices ($\alpha$-H1 and $\alpha$-H2) is called the "Loop domain" (LD). The C-terminal cytoplasmatic tail of HA-2 is not shown.

Figure 1A:
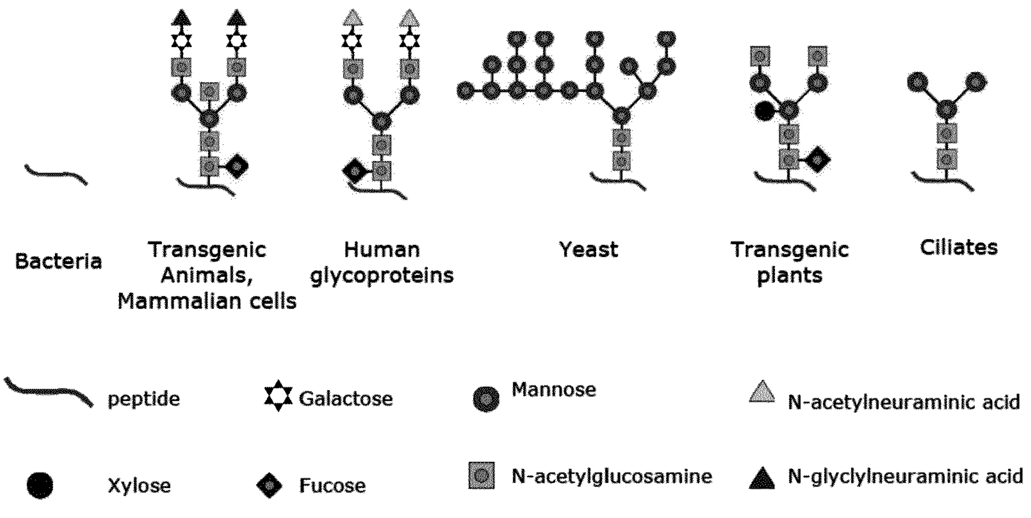
FIG. 1A shows an overview of N-glycosylation patterns of different taxa. Generally, the term "N-glycosylation" refers to glycosylation of the amino acid residue asparagine (N). Here, an oligosaccharide chain is attached by oligosaccharyltransferase to those asparagine residues which occur in the tripeptide sequences Asn-X-Ser or Asn-X-Thr, where X can be any amino acid except Pro.

HA1 comprises a spherical domain ("head") which is stabilized by disulfide bridges not shown. Said head comprises binding sites for sialic acids located in the glycokalyx of the host cell membrane. Likewise, the head has a high immunogenic potential and is thus target for most antibodies generated against HA after immunization.

To elicit the fusion of the virus envelope bilayer with the host cell membrane HA1 and HA2 are separated from one another triggered by a pH decrease, which results in a positive charge of the HA1 subunits in the HA homotrimer.

This leads to repelling forces and the HA1 subunits move away from one another, thereby disenganging from HA2 subunits, which are then activated. The activated HA2 accounts for the fusion of the membranes. HA2 can be activated only once, and later it remains inactive. It is thus important that HA1 disenganges not too early, otherwise the virus loses its infective potential.

HA2 has, over large stretches, an alpha helical structure and contains a large loop region. In addition, HA2 contains the transmembrane domain and the fusion peptide. The fusion peptide is set free by the detachment of HA1 subunits.

In order to release the fusion, the spherical domain ("head") of HA1 must be separated from HA2. Thus, HA2 can change its conformation, so that it unfolds and the fusion peptide can penetrate the host membrane. Thus the virus becomes directly connected to the host membrane.

Because of the unfolding process, HA2 is stretched on one side. Other areas are rolled in, so that there is no net enlargement of the protein. Then, HA changes its conformation and brings the virus near to the host membrane, so that membrane fusion takes place.

FIG. 4A shows the general structure of a Class I viral fusion protein as defined in the text, as exemplified by hemagglutinin. HA1 and HA2 are subunits of an Influenza HA0 Class I protein. Labels specify the positions of the signal peptide (SP), the fusion peptide (FP), processing sites (arrows), the transmembrane domain (TMD) which are subunits of a general Class I viral fusion protein.

In FIG. 4B (see as well SEQ ID 3) the subunits of the hemagglutinin of Influenza A virus strain A/New Caledonia/20/1999H1N1 (GenBank accession number: AAP34324.1) are exemplarily indicated. Underlined passages indicate the signal peptide, (SP), the HA2 Fusion peptide (FP) and the HA2 transmembrane domain (TMD).

The protein shown consists of 565 amino acid residues ("AA"). Specific sequence features are indicated in table 4. Note that the HA2 fusion peptide and the HA2 transmembrane domain have a high share of hydrophobic amino acids (data calculated on the basis of hydropathy data as of table 1), wherein e.g. the fusion peptide comprises 8 glycine residues. The inventors have shown that for heterologous expression purposes in Ciliates, a truncation of these domains, as provided by the present invention, faciliates protein secretion and/or faciliates protein purification after cell lysis.

TABLE 1

| Subunits | Functional domains | AA | Share of hydrophobic AA |
|---|---|---|---|
| Signal peptide | | 1-17 | |
| HA1 chain | | 18-343 | 42 % |
| HA2 chain | | 344-565 | 41 % |
| | HA2 fusion peptide | 344-368 | 71 % |
| | HA2 extracellular domain | 368-529 | |
| | HA2 transmembrane domain | 530-550 | 66.6 % |
| | HA2 intracellular domain | 551-565 | |
| N-glycosylation sites | | 28, 40, 104, 142, 176, 303, 497 | |
| Interchain disulfide bond | | 21-480 | |

Table 1 makes clear that HA2 transmembrane domain and HA2 fusion peptide have the highest share of hydrophobic amino acids. The inventors have deduced from this finding that truncation of at least one of these two domains will facilitate secretion of the protein into the medium.

It is noteworthy that the features shown for the protein in FIG. 4 are applicable to other hemagglutinins as well, as for most Class I Viral fusion proteins shown in table 3.

FIG. 5 shows a comparison between codon usage in *Tetrahymena thermophila* and *Homo sapiens*. The latter is applicable for viral proteins being expressed in a human host, like hemagglutinin expressed from a human host cell. See text for further explanations.

FIG. 6 shows the genetic code as used in ciliates, particularly in *Tetrahymena*. The non-canonical nucleotide codes UAA and UAG, which encode for glutamine, are printed in bold. According to the general genetic code, these tripletts are, however, stop codons (see striked through tripletts). "1LC" stands for "one letter code", whereas "3LC" stands for "three letter code".

Figure 7:
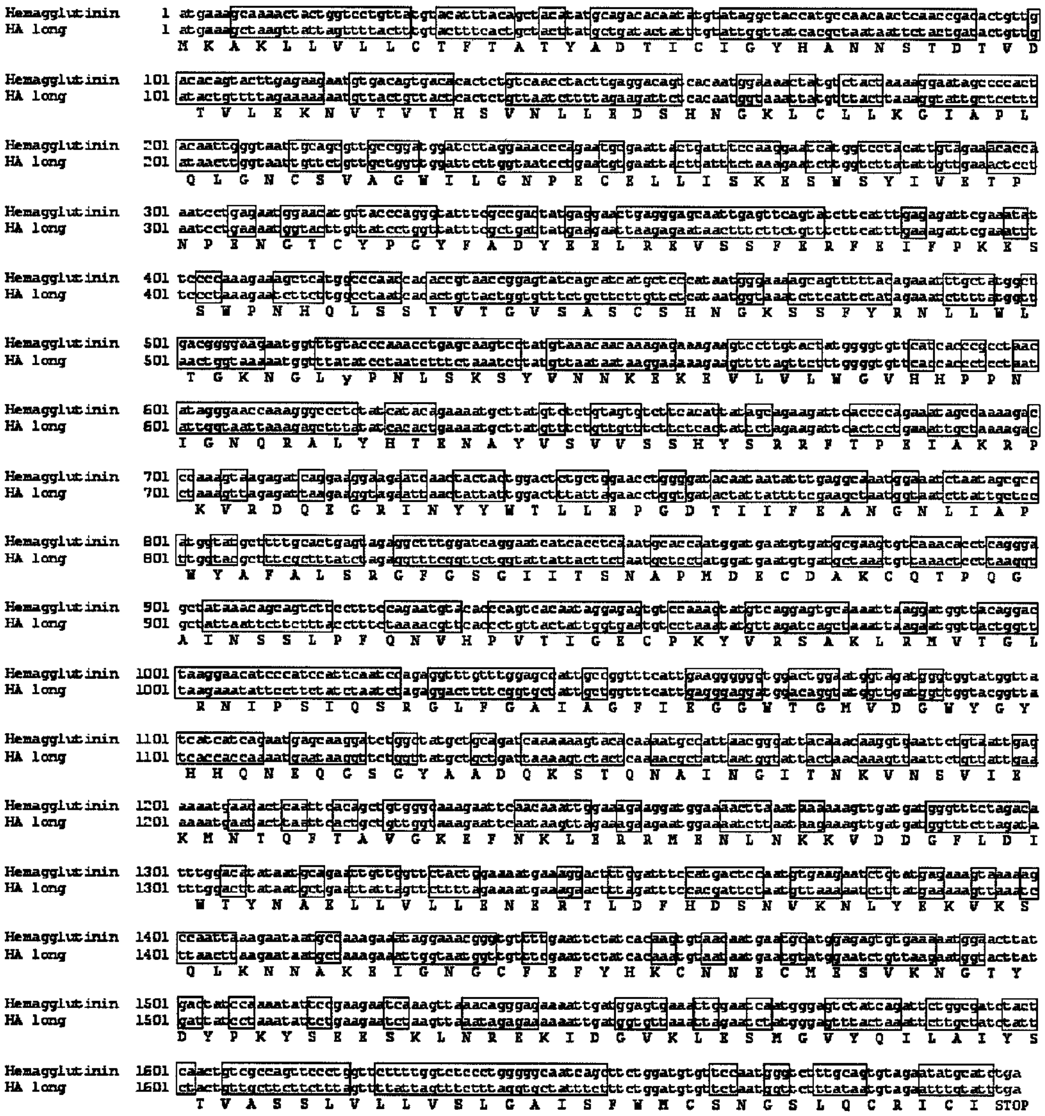

FIG. 7 shows exemplarily the comparison between the codon usage between the viral hemagglutinin sequence (see SEQ ID No. 1) and the codon optimized sequence of hemagglutinin (see SEQ ID No. 2) for an expression in *Tetrahymena thermophila*. Differences in the codon usage are indicated using grey boxes.

Figure 8:
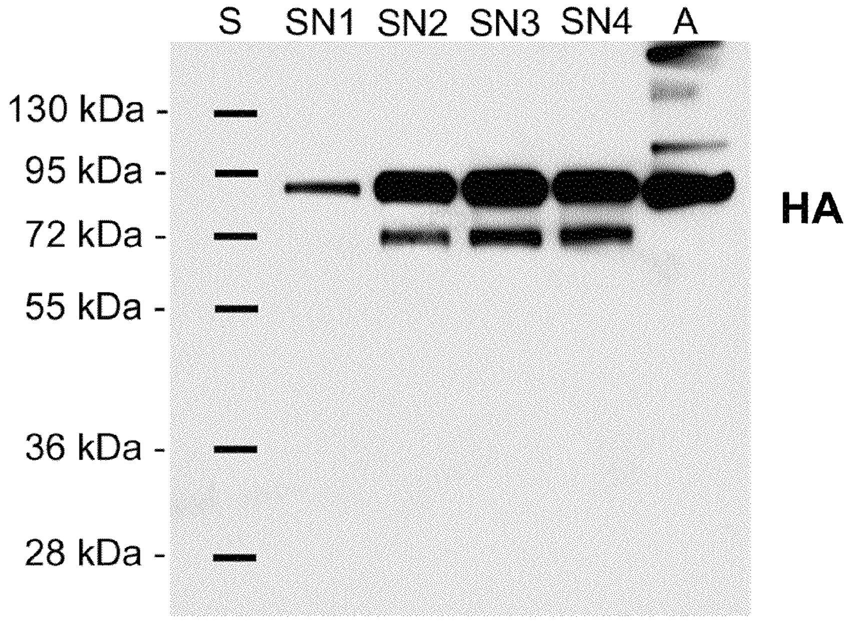

In FIG. 8 immunoblots of transformed ciliates cultivated in a fed-batch fermentation process (0.5 L) expressing recombinant HA are shown. Samples of the supernatant from different points of time of harvest (SN1—47.5 h, SN2—66 h, SN3—70 h, SN4—90 h) were applied to SDS-PAGE under non-reducing conditions followed by Western Blot. Staining took place using a specific Influenza anti-B/Florida/4/2006 serum. The applied NIBSC-HA antigen (positive control) showed a signal corresponding to approximately 90 kDa (A, NIBSC, 45 ng). After 47.5 h of cultivation an HA specific band at approximately 72 kDa and 90 kDa appeared in the supernatant. The said protein corresponds to Seq ID No 9.

Figure 9:
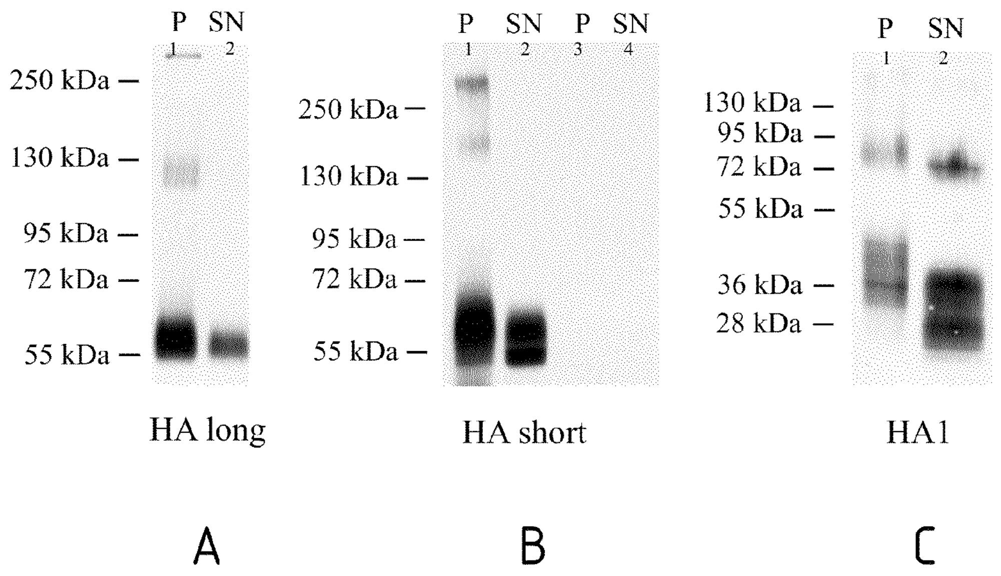

In FIG. 9 immunoblots of hemagglutinin protein fragments of different lengths (truncated according to the teaching of the present invention) recombinantly expressed in *Tetrahymena* are shown. Staining took place using a specific Guinea Pig-anti-H1N1 antibody. P is *Tetrahymena* cell pellet, and SN is cell culture supernatant. Lane 1 and 2 refers to *Tetrahymena* clones while lane 3 and 4 are the wild type control.

FIG. 9A shows a protein called "HA_long", which is a full HA1-HA2-dimer devoid of the intracellular domain (CT, see FIG. 4A) of HA2 (predicted molecular weight 61.4 kDa). The said protein corresponds to Seq ID No 3.

FIG. 9B shows a protein called "HA_short" which is a HA1-HA2-dimer devoid of the intracellular domain (CT) and the hydrophobic transmembrane domain (TMD) of HA2 (predicted molecular weight 57.6 kDa). The said protein corresponds to Seq ID No 5.

FIG. 9C shows mere HA1 (called "HA_1", predicted molecular weight 34.2 kDa), i.e. HA2 with its at least two hydrophobic domains (fusion peptide and transmembrane domain) has been truncated thereof. The said protein corresponds to Seq ID No 7.

It is clear from the immunoblots that HA_short and HA_1, which are devoid of at least one hydrophobic domain are more abundant in the supernatant than HA_long, which supports the conclusion that the protein secretion of viral fusion proteins in ciliates is promoted by removal of at least one hydrophobic domain, because the tendency to attach to cellular membranes is reduced. Furthermore, as the immunogenic domains of viral fusion proteins, particularly hemagglutinin, are located in the HA1 subunit, it is to be expected that a vaccine comprising only the HA1 subunit, or a HA1 subunit plus a truncated HA2 subunit, will still elicit an immune response, and is thus useful for the production of a vaccine.

Figure 10A:
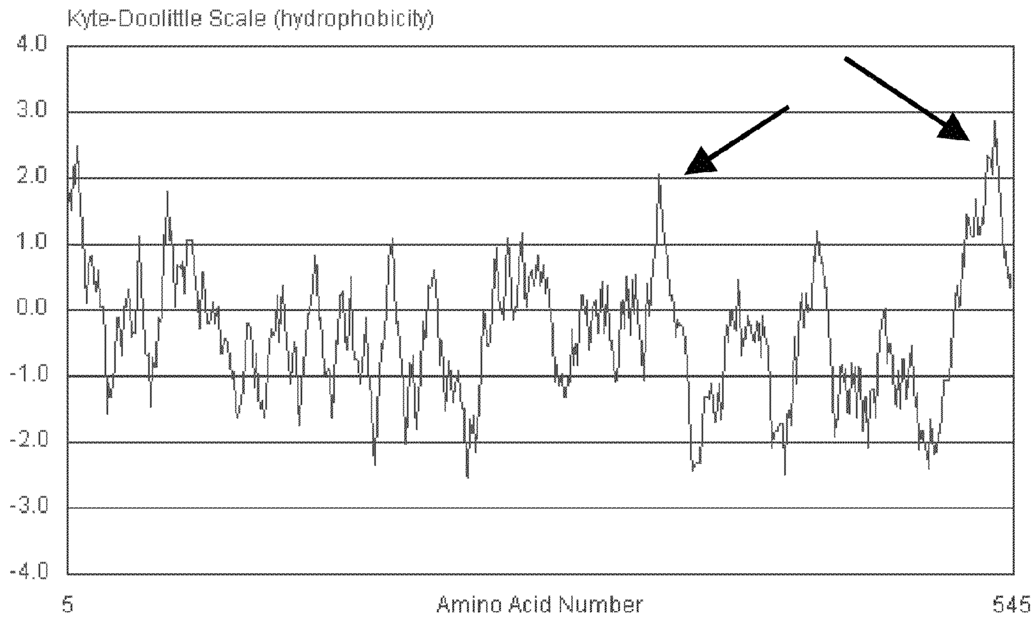
Figure 10B:
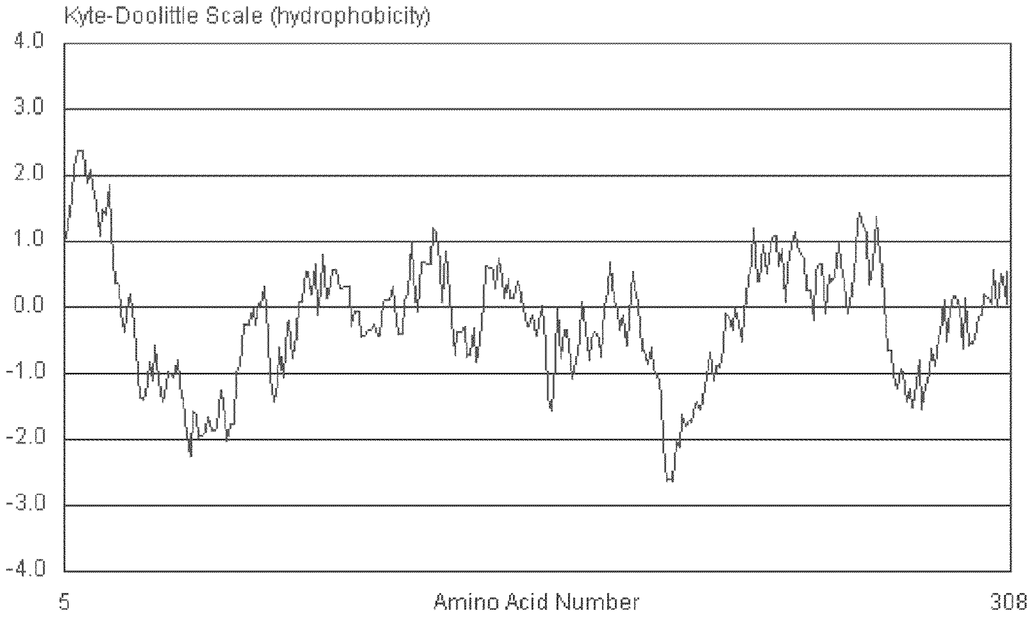

FIG. 10 A shows a hydrophobicity plot of the protein according to Seq ID No 3 (i.e. "HA_long") of the present invention, which has been plotted according to the Kyte-Doolittle scale. It is easily determined that the fusion peptide (AA 344-368) and the transmembrane domain (AA 530-550) are among the major hydrophobic regions of the protein (see arrows), and do thus hinder an efficient secretion of the protein into the medium.

FIG. 10 B shows a hydrophobicity plot of a ciliate major secreted protein (SEQ ID NO 2 of WO03078566 by the inventors of the present invention), which is secreted by *Tetrahymena* in its natural environment in large quantities. It is quite obvious that this protein does not have highly hydrophobic domains and is on average less hydrophobic than HA_long. The inventors make this phenomenon responsible for the ease of secretion of this protein in contrast to HA_long.

DETAILED DESCRIPTION OF INVENTION

A. Definitions

The term "heterologous expression", as used herein, shall refer to the protein expression of a gene, a nucleic acid or a cDNA, which is foreign to the organism in which the expression occurs.

The term "ciliate", as used herein, shall refer to the scientific phylum of Ciliophora, which are unicellular eukaryotes ("protozoa" or "protists") characterized, among others, by their relatively large size (some species have up to 2 mm in length), their ciliated cell surface and by two different sorts of nuclei, i.e. a small, diploid micronucleus, and a large, polyploid macronucleus (transcription active). The latter is generated from the micronucleus by amplification of the genome and heavy editing.

The term "cDNA", as used herein, shall refer to a DNA molecule which encodes for a protein to be expressed, and is devoid of any non-encoding parts, like introns. In many cases, a cDNA has been directly synthesized from an RNA template using reverse transcriptase, and an oligo dT-primer. However, the term shall as well comprise synthetic genes and encoding DNAs otherwise obtained.

The term "promoter", as used herein, shall refer to a regulatory region of DNA generally located upstream (towards the 5' region of the sense strand) of a gene or a cDNA, that contains essential genetic elements which allow or even enhance transcription of the gene, or the cDNA.

The term "fragment", as used herein, shall refer to a part of a protein which lacks some parts, or domains, of the native, or wildtype protein while retaining some activity in terms of enzymatic activity, immunogenity, target binding or the like.

The term "signal sequence", as used herein, shall refer to a nucleic acid sequence which encodes for an oligopeptide ("signal peptide" or "transit peptide") which directs the transport of a protein to certain organelles such as the nucleus, mitochondrial matrix, endoplasmic reticulum, chloroplast, apoplast and peroxisome. Almost all proteins that are transported to the endoplasmatic reticulum have a sequence consisting of 5-10 hydrophobic amino acids at the N-terminus. Those signal peptides are cleaved from the protein by a signal peptidase after the cotranslational insertion of the protein into the luman of the ER. Most proteins are then transported via Golgi apparatus downstream on the secretory pathway.

The term "operably linked" as used herein, means that a nucleotide sequence, which can encode a gene product, is linked to a promoter such that the promoter regulates expression of the gene product under appropriate conditions.

The term "hydrophobic domain" is being used synonymously with the terms "lipophilic domain" and/or "non-polar domain". As used herein, said terms shall refer to a protein domain which has, at least at its periphery, hydrophobic properties (also termed "hydropathy") mainly governed by the abundance of hydrophobic/non-polar amino acid residues, and which has thus some affinity to lipid fractions, as for example phospholipid bilayers as found in cell membranes.

Said hydrophobic domain may for example qualify as a so-called "transmembrane domain", i.e. a three-dimensional protein structure which is thermodynamically stable in a membrane. Such transmembrane domain may comprise a single alpha helix, a stable complex of several transmembrane alpha helices, a transmembrane beta barrel, a beta-helix, an outer ring of hydrophobic amino acids surrounding potentially hydrophilic amino acid residues, and the like.

The inventors have realized that hydrophobic domains may hamper the secretion of a protein into the environment. Examples for hydrophobic amino acids are given in the following table:

TABLE 2

| Amino Acid | Hydropathy index (Kyte & Doolittle 1982) |
|---|---|
| Isoleucine | 4.5 |
| Valine | 4.2 |
| Leucine | 3.8 |
| Phenylalanine | 2.8 |
| Cysteine | 2.5 |
| Methionine | 1.9 |
| Alanine | 1.8 |
| Glycine | −0.4 |
| Threonine | −0.7 |
| Serine | −0.8 |

The term "nucleic acid molecule" is intended to indicate any single- or double stranded nucleic acid molecule comprising DNA (cDNA and/or genomic DNA), RNA (preferably mRNA), PNA, LNA and/or Morpholino.

The term "stringent conditions" relates to conditions under which a probe will preferably hybridize to its target subsequence and much less to other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion (or other salts) at pH 7.0 to 8.3 and the temperature is at least about 30° C. for short probes (e.g. 10 to 50 nucleotides) and at least about 60° C. for longer probes. Stringent conditions may also be achieved with the addition of destabilizing agents, such as formamide and the like.

The term "PDB code" relates to a unique four letter code which serves as the primary identifier by which entries can be retrieved from the Protein Data Bank, which is the worldwide repository of biological macromolecular structural data The term "fragment of the nucleic acid molecule" is intended to indicate a nucleic acid comprising a subset of a nucleic acid molecule according to one of the claimed sequences. The same is applicable to the term "fraction of the nucleic acid molecule".

The term "variant of the nucleic acid molecule" refers herein to a nucleic acid molecule which is substantially similar in structure and biological activity to a nucleic acid molecule according to one of the claimed sequences.

The term "homologue of the nucleic acid molecule" refers to a nucleic acid molecule the sequence of which has one or more nucleotides added, deleted, substituted or otherwise chemically modified in comparison to a nucleic acid molecule according to one of the claimed sequences, provided always that the homologue retains substantially the same properties as the latter.

The term "codon optimized", as used herein, shall refer to a process in which the cDNA encoding the heterologous protein to be expressed is adapted to a host specific codon usage which derives from the universal genetic code scheme. Ciliates have an AT-rich genome, with *Tetrahymena* DNA consisting of approximately 75% AT (see FIG. 7). The codon usage differs from that in other organisms particularly in how often a codon is used to encode a given amino acid ("codon bias"). If the non-optimized cDNA encoding a heterologous protein uses codons which are rarely used in Ciliates this might strongly affect the protein expression efficiency. This means, in turn, that heterologous protein expression can improve dramatically when the codon frequency of the gene under study is matched to that of the ciliate expression system. Moreover, many ciliates, among them *Tetrahymena* utilize non-canonical nucleotide codes with UAA and UAG tripletts encoding for glutamine, while in most other organisms these codons are used as stop codon which terminate translation. This may lead to the fact that foreign (non ciliate) genes carrying UAA and UAG tripletts as stop codon are not correctly expressed. For this purpose, before transforming the ciliate host cell, the cDNA encoding a heterologous protein should be code optimized in such way that UAA and UAG tripletts are amended into UAA. Code optimization can for example be accomplished by site directed mutagenesis, or by de novo cDNA synthesis.

The term "derivative", as used herein, refers to a related nucleic acid molecule that has similar characteristics to a target nucleic acid sequence as a nucleic acid molecule according to one of the claimed sequences.

The term "sequence identity of at least X %", as used herein, refers to a sequence identity as determined after a sequence alignment carried out with the family of BLAST algorithms (particularly megablast, discontiguous megablast, blastn, blastp, PSI-BLAST, PHI-BLAST, blastx, tblastn and tblastx), as accessible on the respective internet domain provided by NCBI.

The term "host cell", as used herein, has two different meanings which may be understood according to the respective context. In the context of heterologous protein expression, the term "host cell" refers to a transgenic cell which is used as expression host. Said cell, or its progenitor, has thus been transfected with a suitable vector comprising the cDNA of the protein to be expressed. In the context of the viral life cycle, the term "host cell" refers to a cell which is infected by a virus which uses the cell for replication.

The term "vector", as used herein, refers to a molecular vehicle used to transfer foreign genetic material into another cell. The vector itself is generally a DNA sequence that consists of an insert (sequence of interest) and a larger sequence that serves as the "backbone" of the vector. The purpose of a vector to transfer genetic information to another cell is typically to isolate, multiply, or express the insert in the target cell.

The term "plasmid", as used herein, refers to plasmid vectors, i.e. circular DNA sequences that are capable of autonomous replication within a suitable host due to an origin of replication ("ORI"). Furthermore, a plasmid may comprise a selectable marker to indicate the success of the transformation or other procedures meant to introduce foreign DNA into a cell and a multiple cloning site which includes multiple restriction enzyme consensus sites to enable the insertion of an insert. Plasmid vectors called cloning or donor vectors are used to ease the cloning and to amplify a sequence of interest. Plasmid vectors called expression or acceptor vectors are specifically for the expression of a gene of interest in a defined target cell. Those plasmid vectors generally show an expression cassette, consisting of a promoter, the transgene and a terminator sequence. Expression plasmids can be shuttle plasmids containing elements that enable the propagation and selection in different host cells.

The term "viral protein", as used herein, refers to proteins generated by a virus. Said proteins may either form the viral envelope and/or the capsid, or may be nonstructural, regulatory and accessory proteins.

The term "surface protein", as used herein, shall refer to virus proteins which form part of the viruses outer layer. Such proteins are, for example, (i) proteins anchored in the lipid bilayer coatings of enveloped viruses, (ii) capsid proteins both in enveloped and non-enveloped viruses and/or (iii) spike proteins as found in many viruses, like bacteriophages and viruses infecting humans, including mammals including birds. The said lipid bilayer coatings of enveloped viruses are in most cases acquired by the virus during its replication cycle, namely upon exocytosis or cell lysis, from intracellular membranes in the host cell (e.g., the inner nuclear membrane, or the golgi membrane), or from the host cells outer membrane.

The term "viral fusion protein", as used herein, refers to glycoproteins of enveloped viruses, which facilitate the infection of host cells (insertion of virus genetic material into the host cell). Enveloped viruses, with a lipid bilayer as integral part of their structure, enter the cells they infect by fusion of the viral and the host cell membrane. Said viral fusion proteins combine two main features: they contain a receptor binding function, which attaches the virus to the host cell and they include a fusion function that can be activated to mediate the fusion of the viral and host cell membrane. Some prominent viral fusion proteins are class I viral fusion proteins (see below).

The term "fusion peptide", as used herein, refers to a distinct conserved hydrophobic region inside of a viral fusion protein which inserts into the host cell membrane during fusion process. Fusion peptides tend to be apolar regions, relatively rich in glycine and alanine residues and containing several bulky hydrophobic residues. For class I viral fusion proteins the fusion peptide is located at the N terminus of the transmembrane region of the protein.

B. Description of the Disclosed System

According to the present invention, a system for the heterologous expression of a viral protein is provided, said system comprising a ciliate host cell, at least one nucleic acid encoding for a viral protein, or a fragment thereof, and a promoter operably linked to said nucleic acid.

In a preferred embodiment, said nucleic acid is a cDNA.

Basically, the heterologous expression of viral proteins is not a common thing today, as viral proteins are, in most cases, structural proteins, i.e., neither enzymes nor protein hormones nor antibodies, and thus not that interesting for pharmaceutical or industrial purposes.

Furthermore, the expression of viral proteins in ciliates has not yet been suggested in the above references. The inventors have realized that for ciliates, unlike as for bacteria or metazoa, no specific viruses are known so far. This might be due to the nuclear dimorphism which is common to ciliates. Another reason for this might be the unusual codon usage and AT-rich genome in Ciliates. The inventors do thus assume that pathogenic viruses of higher organisms cannot amplify in most ciliates e.g. *Tetrahymena.*

The above arguments give reasons for the fact that, so far, no attempts are known to produce viral proteins in ciliates.

The fact that, as known so far, ciliates are not susceptible for viruses, arises as a surprising advantage. This means that in production processes based on Ciliates, amplification or growth of adventitious viruses does not occur. This means, furthermore, that in case a protein is produced for therapeutic use, costly virus depletion procedures as necessary in industrial processes with human and animal cell cultures can be skipped.

Furthermore, promoters suitable for viral protein expression in ciliates are, for example, disclosed in WO2007006812A1 which is also registered for the applicant of the present invention, the content of which shall be incorporated herewith by reference. Seq ID No 12 and 13 of the attached sequence listing give the sequences of two ciliate-specific promotors particularly preferred in the context of the present invention, namely a heat-inducible promoter and a metallothionein-promoter.

It is worth mentioning that Gaertig et al. (1999) (see also EP1151118) have demonstrated the use of the protozoan *Tetrahymena thermophila* as a protein expression system for a surface antigen protein of another protozoan, i.e. *Ichthyophthirius multifiliis*, which is a fish parasite. They report that the protein thus produced is being displayed on the surface of transformed *Tetrahymena* cells, where it can be harvested and being used for the manufacture of a vaccine against *Ichthyophthirius multifiliis*. Another idea is to directly use the transformed *Tetrahymena* cells displaying the antigen on their surface as a live vaccine.

However, the authors suggest that *Tetrahymena* may only be used as a host for the cloning and expression of genes from organisms with AT-rich genomes, i.e. protozoans like *Plasmodium, Mycoplasma*, or *Leishmania*, which are human pathogens as well. Because of the inherent instability of AT tracts in conventional systems such as *Escherichia coli*, cloning genes from these organisms can prove difficult. *Tetrahymena* DNA consists, for example, of approximately 75% AT.

Furthermore, it is reported that expressing foreign genes in *Tetrahymena* is hampered by codon usage problems. *T. thermophila* utilizes UAA and UAG tripletts for glutamine, while in most other organisms these codons are used as stop codons which terminate translation. This may lead to the fact that foreign genes carrying a UAA and UAG triplett as stop codon are not correctly expressed.

In a preferred embodiment according to the invention, the system further comprises a signal sequence operably linked to said nucleic acid, which signal sequence accounts for the secretion of a viral protein encoded by said nucleic acid, or a fragment thereof, into the extracellular medium.

Viral proteins are, when expressed in nature (i.e. by a bacterial host cell infected by a bacteriophage, or by a metazoan host cell infected by a virus), not subject of secretion, as a virus uses the machinery and metabolism of its host to merely produce its own proteins, which are then assembled to second generation viruses before lysis of the host cell. This in turn means that virus proteins have never been under evolutionary pressure to optimize for the ability of being secreted.

This is one reason for the fact that the recombinant production of soluble virus proteins and subsequent secretion of these soluble viral proteins is a complicated matter. Suitable signal sequences are, for example, disclosed in WO03078566A1 which is also registered for the applicant of the present invention, the content of which shall be incorporated herewith by reference.

Seq ID Nos 8 and 10 of the attached sequence listing give the nucleic acid sequences of two signal peptides particularly preferred in the context of the present invention, namely the endogenous signal peptide of the HA gene, and the ciliate phospholipase A1 signal peptide.

In yet another preferred embodiment of the invention, the said viral protein is a viral surface protein, as defined above.

Upon infection of a host, the said viral surface proteins come in contact with the host and do, in some cases, elicit immune responses, if said host allows for such response (e.g., in mammals, which have a well developed immune system). These proteins do thus have the potential to act, in isolated form or in connection with an adjuvant (deactivated virus, or a fragment thereof) as a vaccine.

In yet another preferred embodiment of the present invention, it is provided that the said transgenic ciliate is a member of the family Tetrahymenidae.

In a particularly preferred embodiment, the said transgenic ciliate is *Tetrahymena* sp. (particularly *Tetrahymena thermophila*). *Tetrahymena* is a nonpathogenic unicellular eukaryotic microorganism which has been established in a few laboratories as an expression host. It features a number of advantages which make it suitable for heterologous protein expression. *Tetrahymena* is a broadly examined model organism, and, in over 50 years of basic research, no viruses or endoparasites were observed. Examinations with indicator cell lines revealed no endogenous infectious agents like viruses or mycoplasm, which can infect higher animals.

First of all, the above considerations as related to codon usage in ciliates apply for *Tetrahymena* as well. Furthermore, high copy number plasmids are available for *Tetrahymena*, containing an origin of replication (ori) from a minichromosomal rDNA. This minichromosomal rDNA is present in up to 9,000 copies per cell. Beyond that stable integration can take place into the macronuclear DNA, in which all genes are present in 45-fold copy number. The high gene dose is the ideal precondition for an efficient protein biosynthesis and thus for a high productivity. In contrast to yeasts and bacteria, Ciliates of the genus *Tetrahymena* secrete biologically proteins very efficiently to the fermentation supernatant.

*Tetrahymena* is able to attach posttranslational modifications to proteins, like disulfide bridges, GPI anchor, phosphorylation, acetylation and glycosylation which are more similar to those in mammalian cells than those detected in yeast or other eukaryotic expression systems.

Unlike mammalian cells, *Tetrahymena* combines the ease of growth with short generation times (1.5-3 h), and cost reduction, as chemically defined media can be used and no need for peptides or serum components, like growth factors, exists.

Batch, fed-batch and continuous fermentation of *Tetrahymena* with cell densities up to $2\times10^7$ cells/ml and dry weights of up to 80 g/L are established, and production enlargements (upscaling) up to 1000 L could be demonstrated without any problem. In feasibility studies with reporter proteins space-time yields of 50-90 pg/cell a day could already be achieved. First experiments with homologous expression resulted in a yield of over 200 mg/L a day for secreted proteins. *Tetrahymena* can be fermented in conventional production facilities for microbiological expression systems (bacteria or yeasts). This means that no costly modifications in existing production plants or a new building of the production facilities are necessary.

Despite the said advantages, ciliate expression systems, particularly *Tetrahymena*, are still relatively unknown, and the person skilled in the art, when being asked about potential heterologous protein expression systems, would rather think of *E. coli*, yeasts, baculovirus-based systems and immortalized mammal cell lines.

Yet, the use of a ciliate expression system, particularly *Tetrahymena*, has another significant advantage which was not foreseeable in the present context. As the self/non-self discrimination of mammalian immune systems is realized on the basis of carbohydrate composition of the glycoproteins, the glycosylation pattern of an antigen contributes, to a large extent, to its immunogenic potential.

Reading et al. (2000) have reported that, in mammalian cells, the mannose receptor plays a role as a major endocytotic receptor in the infectious entry of influenza virus, and perhaps other enveloped viruses, in macrophages.

The mannose receptor can be qualified as a membrane bound lectin protein (also termed “mannose binding lectin”, “MBL”) which mediates the uptake of glycoproteins terminating in mannose, fucose or N-acytylglucoseamin and C-type lectins containing conserved carbohydrate recognition domains (CRD).

The CRD of the mannose binding lectin (MBL) binds hexoses such as mannose and N-acetylglucoseamin with equitorial hydroxyl groups at the position C3 and C4 of the pyranose ring. They have thus no affinity for oligosaccharides commonly found on mammalian glycoproteins.

Macrophages play a key role in mammalian immune systems, as they take up pathogens by endocytosis and, after digesting the latter, present pathogen-related antigens to the corresponding helper T-cells. The presentation is done by integrating the antigen into the cell membrane and displaying it attached to a MHC Class II molecule to a corresponding helper T cell, indicating to other white blood cells that the macrophage is not a pathogen, despite having antigens on its surface.

The inventors have deduced, from the research of Reading et al. (2000), that, in order to enhance the immunogenicity of a vaccine, it might be helpful to increase the amount of mannose in the glycosylation patterns of proteins comprised in the vaccine (i.e. to enhancing the mannosylation). Protein glycosylation is however carried out in the posttranslational modification apparatus, which is exclusive to eukaryotes, and thus difficult to modify by design.

However, eukaryote taxa show differences in their glycosylation schemes, particularly in N-glycosylation schemes. The said glycosylation occurs mainly in eukaryotes and archea, but not in bacteria. Generally, the term N-glycosylation refers to glycosylation of asparagine (N) amino acid residues. Here, an oligosaccharide chain is attached by the enzyme oligosaccharyltransferase to those asparagine residues which occur in the tripeptide sequences Asn-X-Ser or Asn-X-Thr, where X can be any amino acid, although Pro and Asp are rarely found.

Figure 1B:
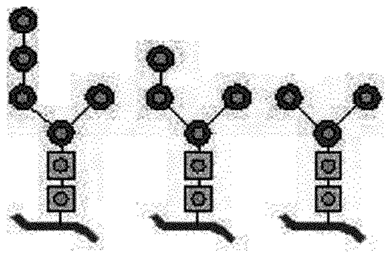
FIG. 1*b* shows potential variations in the said pattern in some ciliate species.

The inventors of the present invention have surprisingly realized that Ciliates have a unique N-glycosylation pattern, bearing a high degree of mannose residues (see FIG. 1). It is furthermore the merit of the inventors of the present invention that they found that proteins which are to be used for vaccination in mammals might benefit from terminal mannose residues, namely due to the increased capturing of these proteins in macrophages via the mannose receptors which might result in an increased immune response.

The inventors have thus deduced that proteins expressed in ciliates, particularly in *Tetrahymena*, have a higher immunogenic potential due to a high degree of mannose residues, and that transgenic ciliates are thus promising candidates for the production of vaccines, particularly virus vaccines, for use in mammals.

The inventors have furthermore realized that macrophages demonstrated an increased phagocytosis of pathogens which have a mannose-rich glycosylation pattern. For this reason, there is evidence that the expression of vaccines in ciliates will, due to the mannose rich glycosylation pattern, lead to an enhanced immune reaction once the vaccines thus produced are administered to a mammalian subject.

As indicated above, viral fusion proteins are subdivided into Class I, Class II and Class III viral fusion proteins. Table 3 gives an overview of some viral fusion proteins from enveloped viruses which meet the above definition.

Therein, "-S-S-" indicates a disulfide bridge, whereas "/" indicates that the indicated subunits are associated to one another, but not disulfide-bonded. "GPX" or "gpX" stands for "glycoprotein X", whereas "FX" stands for "fusion protein X".

TABLE 3

| virus family | Example virus species | Example proteins | PDB code | Viral Fusion Protein/ fusion subunits |
|---|---|---|---|---|
| | | Class I | | |
| Orthomyxo-viridae | Influenza A virus (HA) Influenza C virus (HEF) | HA1, HA2, HEF1, HEF2, | 1HA0, 1FLC | HA1-S-S-HA2 |
| Retroviridae | Moloney murine leukemia virus (TM) | TM, SU | 1AOL | SU-S-S-TM |
| | human immunodeficiency virus | HIV-1 gp41, gp120 gp21 | ENV, 1AIK 1MGI | gp120-S-S-gp41 |
| Paramyxo-viridae | Simian parainfluenza virus 5 (F) human parainfluenza virus F newcastle disease virus F respiratory syncytical F | F1, F2 | 2B9B, ISVF IZTM 1G5G 1G2C | F2-S-S-F1 |
| Corona-viridae | Mouse hepatitis virus S2 SARS corona virus E2 | S1, S2 | 1WDG 2BEQ | S1/S2 |
| Filoviridae | Ebola virus gp2 | GP1, GP2 | 1EBO, 2EBO | GP1-S-S-GP2 |
| | | Class II | | |
| Arena-viridae | Junin virus | GP1, GP2 | | GP1/GP2/SSP |
| Toga-viridae | Semliki forest virus E1 | E1, E2 | 1E9W, 1RER | E1/E2 |
| Flavi-viridae | Tick-Borne Encephalitis Virus (E) Dengue 2 and 3 virus E | E | 1URZ, 1SVB 1OK8, 1UZG | E, E1/E2f |
| Bunya-viridae | Crimean-Congo-Haemorrhagic-Fever (CCHF) | GN, GC | | GN/GC |
| | Hantaan virus (HTNV) | G1, G2 | | |
| | | Class III | | |
| Rhabdo-viridae | Rabies virus vesicular stomatitis virus | G proteins | 2GUM | G |
| Herpes-viridae | Herpes simplex virus gB | gB, gD, gH/L | 2CMZ | gB, gH/L |

This finding is not anticipated by the work of Gaertig et al. (1999, see above), as the latter have only described the use of a ciliate protein produced in a transgenic *Tetrahymena* for use as a vaccine in fish. However, the above described effect of the mannose receptor in macrophages is according to current knowledge only applicable for mammals, not for fish. For this reason, it is quite unlikely that a fish vaccine would draw similar benefit from an increased mannose amount in the glycosylation pattern of the vaccine.

In a particularly preferred embodiment, the said viral surface protein is a viral fusion protein (see definition above).

In yet another preferred embodiment, the said viral surface protein is at least one viral fusion protein selected from the group consisting of Class I, Class II and/or Class III Viral Fusion Proteins.

Said viral fusion proteins are structurally quite diverse, but their fusion subunits ultimately fold back into a trimer-of-hairpins, in which three C-terminal regions pack on the outside of a central N-terminal trimeric core.

Very often, two or more subunits of a Class 1 Viral fusion protein are linked by a disulfide bridge, or by other means. Examples for such dimers are HA1-S-S-HA2, SU-S-S-TM, HA1-S-S-HA2, SU-S-S-TM, SU/TM, F2-S-S-F1, S1/S2, GP1-S-S-GP2, GP1/GP2/SSP. Therein, at least one subunit is dominated by hydrophobic domains, as for example the HA2 subunit in the HA1-S-S-HA2 construct.

In a preferred embodiment, the said protein is a Class I viral fusion Protein. See FIG. 4 for a schematic of a Class I viral fusion protein.

A particularly preferred viral protein is hemagglutinin. Hemagglutinin (HA) is an antigenic glycoprotein consisting of two Class 1 Membrane Fusion protein subunits, namely HA2 and HAL which is found on the surface of influenza viruses (Orthomyxoviridae) as well as many other bacteria and viruses.

Hemagglutinin is responsible for binding the virus to the cell that is being infected. Today there are known at least 16 different HA subtypes, labeled H1-H16. The first three hemagglutinins, H1, H2, and H3, are found in human influenza viruses, while the avian flu virus has, for example, a H5 hemagglutinin.

The main function of HA is the recognition of target vertebrate cells, accomplished through the respective sialic acid-containing receptors on the target cell membrane, and the entry of the viral genome into the target cells by causing the fusion of the target cell membrane with the viral membrane. In this context, it is worth to be mentioned that Orthomyxoviridae have a phospholipid membrane which encloses the nucleocapsid, said membrane being acquired from the host cell upon release from the latter.

HA is a homotrimeric integral membrane glycoprotein. It is shaped like a cylinder, and is approximately 135 Å long. The three identical monomers that constitute HA are constructed into a central α helix coil; three spherical heads contain the sialic acid binding sites. HA monomers are synthesized as precursors that are then glycosylated and cleaved into two smaller polypeptides, i.e. the HA1 and HA2 subunits. Each HA monomer consists of a long, helical chain anchored in the membrane by HA2 and topped by a large HA1 globule (see FIG. 3).

The binding mechanism is as follows: HA binds to the monosaccharide sialic acid which is present on the surface of its target cells. This causes the viral particles to stick to the cell's surface. The cell membrane then engulfs the virus and pinches off to form a new membrane-bound compartment within the cell, called endosome, containing the engulfed virus. The cell then digests the content of the endosome by acidifying its interior and transforming it into a lysosome. However, a low pH (<6.0), triggers conformational changes of the HA molecule, in which HA1 separates from HA2 and then refolds into a entirely different shape. In the end of this process the so-called "fusion peptide" acts like a molecular hook by inserting itself into the endosomal membrane and locking on. As soon as the rest of the HA molecule refolds into a new structure (which is more stable at the lower pH), it retracts the "grappling hook" and pulls the endosomal membrane right up next to the virus particle's own membrane, causing the two to fuse with one another. Once this has happened, the contents of the virus, including its RNA genome, are free to pour out into the target cell cytoplasm.

The inventors found that the expression as soluble protein (intracellular expression) as well as the secretion (extracellular expression) of a full hemagglutinin in *Tetrahymena* turned out difficult. While in preliminary experiments, protein expression into the cell membrane as such was successful, the expression of soluble protein and the secretion thereof posed problems as, hemagglutinin molecules successfully expressed in *Tetrahymena*, and equipped with a signal peptide, appeared to remain attached to intracellular membrane structures as well as to the cell membrane of the host cell.

This finding was despite the use of signal peptides which have turned out useful in the expression and secretion of other proteins, as for example shown in WO03078566, which is incorporated herein by reference.

The inventors have attributed this phenomenon to the highly hydrophobic domains, particularly of HA2, which may be responsible for retaining the proteins successfully expressed in the cell membrane.

This phenomenon is thought to be similar to the natural replication process of virus particles in an infected host cell, wherein most viral proteins expressed by the infected host are used to assemble the virion within the cytoplasm, while hemagglutinin is carried via endoplasmatic reticulum and golgi apparatus to the cell surface, where it remains anchored in the cell membrane, until the mature virus buds off from the cell in a sphere of host phospholipid membrane (former host cell membrane), thus acquiring its hemagglutinin coat.

In yet another preferred embodiment of the present invention, it is provided that the viral fusion protein, or the fragment thereof, encoded by the said nucleic acid, is devoid of at least one hydrophobic domain, or a fraction thereof.

In the context of the present invention, the inventors have surprisingly found that a viral protein devoid of at least the hydrophobic fusion peptide domain, or a fraction thereof, facilitates protein secretion.

In heterologous protein expression, protein secretion is supported by a signal sequence (see above). A large hydrophobic domain may cause problems when it comes to protein secretion, as it may exert some affinity to the cell membrane, or to intracellular membranes, of the expression host. Basically, protein secretion in transgenic ciliates like *Tetrahymena* is quite easily attained, as the latter secrete large quantities of hydrolytic enzymes for extracellular digestion of foods. However, it turned out that secretion of full scale viral surface proteins in Ciliates may become cumbersome.

The inventors have now found that removal of a hydrophobic domain does in such cases help to facilitate protein secretion, and to obtain high yields of secreted protein, without affecting the immunogenic potential of the protein thus modified.

In viral proteins, the antigenic domains are often hydrophilic, as they extend from the virus surface into the surrounding medium, which is often an aqueous medium (saliva, blood, mucus and other body fluids, sewage waters, and so forth). This means that a removal of hydrophobic domains does, in these cases, not affect the immunogenicity of the protein.

The said principle of removing a hydrophobic domain in a viral protein in order to facilitate protein secretion or facilitate protein purification after cell lysis, while retaining the protein immunogenicity, will be demonstrated with hemagglutinin (HA) in the following:

In HA protein expression mentioned, HA0 is a precursor protein, consisting of two subunits HA1 and HA2 encoded by a respective cDNA. HA0 is cleaved by proteolytic enzymes (e.g. a tryptase as found in lung tissue of many vertebrates) into its subunits, which remain linked to one another by a disulfide bridge (HA1-HA2-protein, see FIGS. 3 and 4).

While HA1 is responsible for receptor recognition, and comprises the domains with the highest immunogenic potential, particularly a spherical domain ("head") which comprises binding sites for sialic acids located in the glycokalyx of the host cell membrane, HA2 (which also anchors the complete HA 1-HA2 complex in the viral membrane) is responsible for membrane fusion. HA2 comprises an N-terminal fusion peptide (FP) which consists of a relatively hydrophobic sequence (see table 2).

This fusion peptide consists of about 24 N-terminal, highly conserved residues, of which at least six are glycines (see FIG. 4, where the fusion peptides comprises eight glycines). Three α-helices (α-H1, α-H2 and α-H3) follow. A highly hydrophobic transmembrane domain (TMD) follows, which anchors the protein in the lipid bilayer of the viral envelope (see FIG. 3).

The following table, wherein "TMD" stands for "transmembrane domain", and "FP" stands for "fusion peptide", gives an overview about possible modified hemagglutinins devoid of at least one hydrophobic domain, in accordance with the present invention. It is quite clear from the above that the said principle applies as well to other Class I, Class II and/or Class III viral fusion proteins.

TABLE 4

| Example | HA1 | HA2 | Alias name/ Seq ID No |
|---|---|---|---|
| 1 | non-truncated | C-terminally truncated | "HA_Long", SeqID No 2 and 3 |
| 2 | non-truncated | TMD removed | „HA_Short", Seq ID No 4 and 5 |
| 3 | non-truncated | Complete HA2 (inclusive of FP) removed | „HA_1", Seq ID No 6 and 7 |
| 4 | Reduced to the spherical domain ("head") | Complete HA2 (inclusive of FP) removed | |

It is noteworthy to mention that, as an alternative to protein secretion, the inventors found that the intracellular expression of a viral protein in a form that is soluble in the cytoplasm is a promising option. The inventors have found that full-featured Class I viral fusion proteins expressed intracellularly will tend to attach to intracellular membranes of the ciliate host, of which there are many (endoplasmatic reticulum, golgi, nuclear membrane, mitochondria, and so forth), as well as to the cellular membrane, and can in this case not be isolated after lysis of the host cells. The inventors have furthermore found that viral fusion proteins will exhibit reduced tendency to attach to intracellular membranes if they are devoid of at least one hydrophobic domain. Proteins modified in such way (e.g. as shown in Table 4) are thus easier to isolate from whole cell lysates.

Furthermore, according to the invention at least one nucleic acid molecule is provided, the latter selected from the group consisting of a) a nucleic acid molecule comprising a nucleotide sequence presented as SEQ ID NO: 2, 4, and/or 6, b) a nucleic acid molecule encoding a polypeptide comprising the amino acid sequence presented as SEQ ID NO: 3, 5 and/or 7, wherein said polypeptide is a viral protein, or a fragment thereof, c) a nucleic acid molecule encoding a truncated form of a viral protein devoid of at least one hydrophobic domain, preferably of a viral fusion protein, and more preferably of a Class I, Class II and/or Class III viral fusion protein, d) a nucleic acid molecule encoding a truncated form of a Class I viral fusion protein devoid of the transmembrane domain (TMD), the fusion peptide (FP) and/or the HA2 subunit, e) a nucleic acid molecule that is a fraction, variant, homologue, or derivative of the nucleic acid molecules of a)-d), f) a nucleic acid molecule that is a complement to any of the nucleic acid molecules of a)-e), g) a nucleic acid molecule that is capable of hybridizing to any of the nucleic acid molecules of a)-f) under stringent conditions, h) a nucleic acid molecule which comprises, in comparison to any of the nucleic acid molecules of a)-g) at least one silent single nucleotide substitution, i) a nucleic acid molecule according to a) and c)-h) which is code optimized for a protozoan expression host, and/or j) a nucleic acid molecule having a sequence identity of at least 70%, preferably 95% with any of the nucleic acid molecules of a)-i).

Particularly preferred fallback positions for the said nucleic acid molecule have a sequence identity of 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% with any of the nucleic acid molecules of a)-i).

Furthermore, a vector for the transfection of a ciliate host cell is provided, said vector comprising a) a nucleic acid encoding for a viral protein, or a fragment thereof, and b) a promoter operably linked to said nucleic acid.

The said nucleic acid is preferably a cDNA.

The invention furthermore provides a ciliate host cell transfected with a vector according to the invention. Said ciliate is preferable a member of the family Tetrahymenidae.

Furthermore, the invention provided a process for the production of at least one viral protein, or a fragment thereof, in a ciliate host cell, said process comprising the steps of a) transfecting the ciliate host cell with the vector according to the invention, b) culturing the host cell under conditions which allow expression of a protein.

Said process further comprises, in a preferred embodiment, a step of c) culturing the host cell under conditions which allows secretion of the expressed protein of a protein.

Furthermore, the invention provides a protein selected from the group consisting of a) a protein encoded by a nucleic acid according to the invention.

b) a protein comprising the amino acid sequence according to the invention c) a protein according to a) or b) which comprises at least one conservative amino acid substitution, and/or d) a protein obtainable by the process according to the invention.

Furthermore, the invention provides a method for the production of a pharmaceutical composition, said method comprising the steps of a) expressing a protein according to the invention in a ciliate expression system according to the invention, and b) isolating and/or purifying the protein thus obtained.

In an alternative embodiment, the invention provides a method for the production of a pharmaceutical composition, said method comprising the process according to the invention.

Furthermore, the invention provides a pharmaceutical composition comprising a protein according to the invention, or being produced with a method according to the invention. Said composition is, in a preferred embodiment, a vaccine.

Disclaimer

To provide a comprehensive disclosure without unduly lengthening the specification, the applicant hereby incorporates by reference each of the patents and patent applications referenced above.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

Examples

Additional details, features, characteristics and advantages of the object of the invention are disclosed in the subclaims, and the following description of the respective figures and examples, which, in an exemplary fashion, show preferred embodiments of the present invention. However, these drawings should by no means be understood as to limit the scope of the invention.

1. Construction of Expression Vectors

Figure 2A:
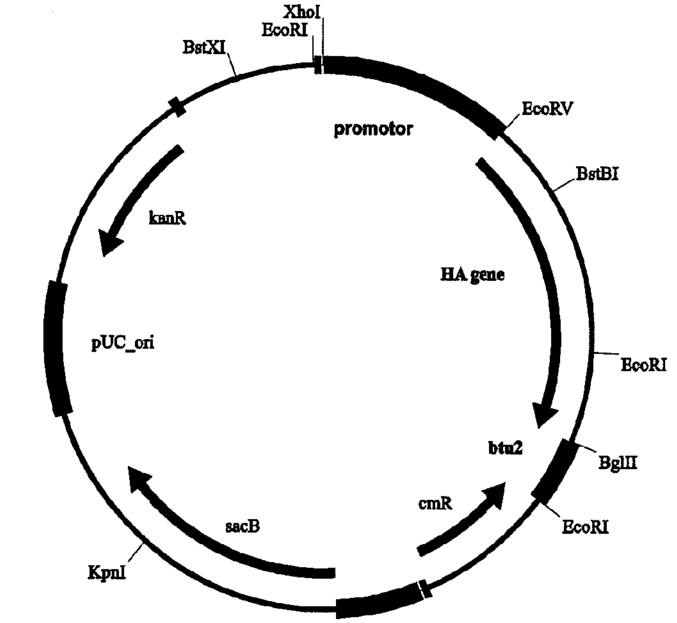
FIG. 2A shows the donor vector encoding the synthetic HA gene. The donor vector consists of a bacterial backbone for amplification in *E. coli* (pUC_ori), a kanamycin (kanR), chloramphenicol (cmR) selection cassette and sucrase gene (sacB) for the selection in *E. coli* and an open reading frame of the target gene (HA gene) under the control of an inducible promoter and followed by *T. thermophila*'s [beta]-tubulin 2 terminator sequence (btu2).
Figure 2B:
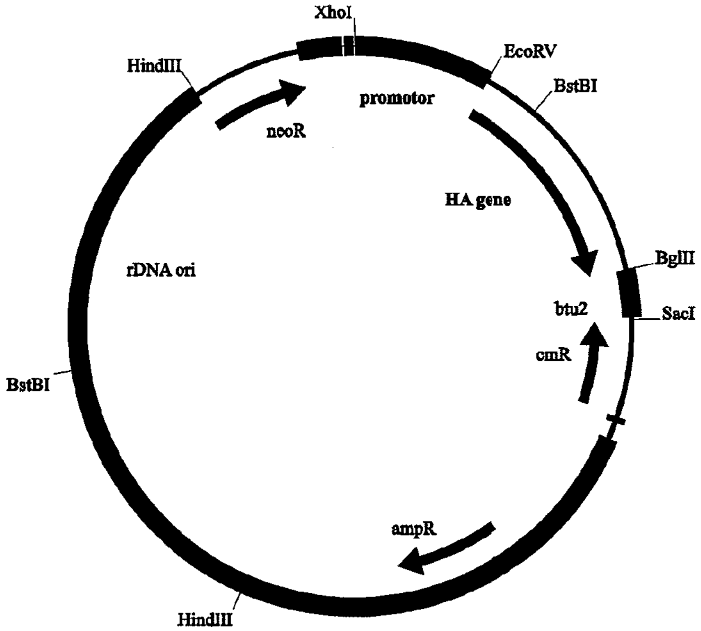
FIG. 2B shows an expression vector for the use in the ciliate *Tetrahymena thermophila*. The vector contains an ampicillin (ampR) and chloramphenicol (cmR) resistance gene for selection in *E. coli*, a *T. thermophila* specific origin (rDNA ori) for plasmid propagation in *T. thermopila*, a neomycin based selection cassette (neoR) for identification of transformed ciliates and an open reading frame of the target gene (HA gene) under the control of an inducible promoter and followed by *T. thermophila*'s [beta]-tubulin 2 terminator sequence (btu2).

The synthetic genes for the different hemagglutinin fragments (see SEQ ID No. 2, 4 and 6) were cloned into the donor vector (see FIG. 2A). The expression cassettes from all donor vectors were transferred into the acceptor vector (see FIG. 2B) using a Cre dependent recombinase system.

2. Cultivation of Wildtype *Tetrahymena* and Transformation of Expression Plasmids Wildtype *Tetrahymena thermophila* strains (e.g. B 1868/4, B 1868/7 and B 2068/1) were cultivated in skimmed milk medium, in supplemented protease peptone (SPP) or in chemically defined medium (CDM). The transformation of the *T. thermophila* cells was performed as previously described in Cassidy-Hanley et al. 1997.

3. Detection of Recombinant Hemagglutinin

Transformed *Tetrahymena* cells were cultivated in SPP medium under selection pressure at 30° C. in a shaker at 80 rpm. Target gene expression was induced by heat shock at 41° C. (HSP-P) or by addition of 20 nM $Cd^{2+}$ (MTT1-P) of logarithmically growing cultures.

Aliquots of transformed cells and of cell free SPP supernatants were harvested 24 h after induction of target gene expression. Collected cells were solubilized in ice cold RIPA-buffer (5000 cells/μl in 150 mM NaCl, 10 mM TrisHCl, 5 mM EDTA, 0.1% SDS, 0.1% DOC, 1% Triton X100, E64 2.5 μg/ml) and disrupted for 15 minutes in a sonicator. SDS-PAGE and Western blot analysis were done according to the art. Briefly, aliquots of either disrupted cells (i.e. 1000 cells) or cell free supernatant were resuspended in Laemmli sample buffer (125 mM Tris HCl pH 6.8, 10% Glycerol, 4% SDS) and separated on 12% SDS-PAGE. The gels were blotted to nitrocellulose membranes and blocked in PBS containing 0.05% Tween 20 and 5% skim milk or 3% bovine serum albumin. The expression of recombinant hemagglutinin in transformed Ciliates was detected using virus strain specific primary antibodies. After washing with PBS/T and applying the secondary HRP-conjugated antibody the blots were developed using Super Signal West Pico Chemoluminescent Substrate (Perbio, Fischer Scientific) in combination with conventional X-ray film development. FIG. 8 and FIGS. 9 A-C show representative Western blots of cell lysates and supernatants of transformed *Tetrahymena* cells after the induction of target gene expression. The wild type control (FIG. 9B, lane 3 cell pellet and 4 supernatant) is all blank. In FIG. 8 the secretion of an HA antigen into the supernatant during the fermentation process is shown. In FIG. 9 the detection of truncated hemagglutinins (removal of intracellular domain (FIG. 9A, "HA_long"), additional removal of transmembrane region (FIG. 9B, "HA_short") and removal of the whole HA2 subunit (FIG. 9C, "HA_1") in the supernatant of transformed ciliates is shown.

4. Production of Hemagglutinin

For fermentations a Braun UD50 (50 Liter) and a Infors Sixfors (0.5 Liter) equipped with standard Rushton impellers were used. Stirrer speed was limited to 300 and 400 rpm; pO2 was set to 20% and pH was set to 7.0 respectively. Fermentations were carried out in standard medium.

5. Purification of Recombinant Hemagglutinin

The harvest of the cells from the 50 L fermentation process was achieved using a hollow fiber module (0.3 $m^2$, 3 L/min, tube diameter 11 mm) to separate the cells from the fermentation broth. The cell pellet was washed 3 to 4 times using ice cold sodium phosphate buffer pH 7.4 (10 mM, PB) and pelleted by centrifugational steps at 10° C. and 2400×g for 8 min (Sorvall evolution, SLA-1500 rotor) to remove mycocyst content. The obtained cell pellet was resuspended in PB supplemented with the cysteine protease inhibitor E-64 (70 μM) and 3% Tween®20. Cells were disrupted using an ultraturrax (IKA UT T25+S25N-25G) at 10,000 rpm for 5 min on ice. The lysate was filled up to 1.8 L using the PB (pH 7.4) and solubilized by stirring at 4° C. for 17 hours. Filtration of the cell lysate took place using a hollow fiber module (0.45 μm with 850 $cm^2$ surface) which was washed three times with 2.3 L of PB (pH 7.4).

Chromatographic purification was performed using a three-step chromatographic purification process which resulted in a highly purified recombinant HA antigen that is not denatured and suitable as a component of a vaccine.

All chromatography was performed at 4° C. The HA containing filtrate prepared as described above was first loaded at 15 mL/min to an ammonium anion exchange column (Capto™ Q column, an agarose bead column with strong quaternary ammonium) equilibrated with PB containing 5% glycerol and 3% Tween®20 at pH 7.4. The column was first washed with loading buffer containing 3% Tween®20 followed by a washing step with loading buffer without Tween®20 to remove the detergent. The elution of the partially purified HA was done using PB containing 5% glycerol and 150 mM NaCl in a first step and 1 M NaCl in a second step (pH 7.4). Samples of all collected fractions were analyzed by SDS-PAGE, Western Blot and Bradford assay and HA positive fractions were pooled for the next chromatography step.

A Ceramic Hydroxyapatite column (CHT) was used to remove contaminating proteins, because the recombinant HA can not bind to this column. The pooled fractions obtained from the Capto™ Q column were concentrated, and a buffer exchange to remove the NaCl was performed using a labscale TFF module (30 kDa) with PB containing 5% glycerol. The pH of the sample was adjusted to 7.5 prior to loading to the CHT column. The loading flow rate was 7 mL/min and the column was washed subsequently with PB containing 5% glycerol. The elution was performed by applying 150 mM PB containing 5% glycerol at pH 7.5 by a step elution. The eluate and the flow through were tested by SDS-PAGE, Western blot analysis and Bradford assay and the HA containing flow through of 200 mL was taken to load to the third column. For the third purification step a Con A Sepharose 4B column (an affinity medium with concanavalin A coupled to Sepharose 4B by the cyanogen bromide method) was used. The flow through of the hydroxyapatite column was supplemented with 150 mM NaCl and applied with a flow rate of 5 mL/min to the column. The column was washed with phosphate buffered saline (PBS, pH 7.4) and the purified recombinant HA was eluted using PBS containing 0.5 M Methyl-α-D-mannopyranoside (pH 7.4). Samples of the elution fractions were analyzed by SDS-PAGE, Western blot and Bradford assay.

TABLE 5

| Seq ID NO | Description | Composition | Alias |
|---|---|---|---|
| 1 | NA sequence of a full HA gene (H1N1 strain A/New Caledonia/20/99) | HA1-HA2, devoid of HA2 intracellular domain | |

TABLE 5-continued

| Seq ID NO | Description | Composition | Alias |
|---|---|---|---|
| 2 | codon optimized version of Seq ID NO 1 | | |
| 3 | AA sequence encoded by Seq ID 3 | | HA_long |
| 4 | NA sequence (codon optimized) of a truncated fragment of Seq ID NO 2 | HA1-HA2, devoid of HA2 intracellular domain and trans-membrane domain | |
| 5 | AA sequence encoded by Seq ID 6 | | HA_short |
| 6 | NA sequence (codon optimized) of a further truncated fragment Seq ID NO 2 | mere HA1, i.e. devoid of HA2 | |
| 7 | AA sequence encoded by Seq ID 6 | | HA_1 |
| 8 | NA sequence of phospholipase A1 signal peptide of *Tetrahymena thermophila*. | | |
| 9 | AA sequence encoded by Seq ID 8 | | |
| 10 | NA sequence of the HA gene endogenous signal peptide | | |
| 11 | AA sequence encoded by Seq ID 10 | | |
| 12 | NA sequence of a heat-inducible promoter of *Tetrahymena thermophila* | | PLA_P |
| 13 | NA sequence of a metallothionein-promoter of *Tetrahymena thermophila* | | MTT1_P |
| 14 | NA sequence of a full HA gene (strain B/Florida/4/2006) | full HA | |
| 15 | AA sequence encoded by Seq ID 14 | | HA |

REFERENCES

Cassidy-Hanley, D.; Bowen, J.; Lee, J.; Cole, E.; VerPlank, L.; Gaertig, J.; Gorovsky, M. & Bruns, P. Germline and somatic transformation of mating *Tetrahymena thermophila* by particle bombardment. *Genetics,* 1997, 146, 135-47.

Gaertig, J.; Gao, Y.; Tishgarten, T.; Clark, T. & Dickerson, H. Surface display of a parasite antigen in the ciliate *Tetrahymena thermophila. Nat Biotechnol,* 1999, 17, 462-5.

Kulakosky, P.; Hughes, P. & Wood, H. N-Linked glycosylation of a baculovirus-expressed recombinant glycoprotein in insect larvae and tissue culture cells. *Glycobiology,* 1998, 8, 741-5.

Reading, P.; Miller, J. & Anders, E. Involvement of the mannose receptor in infection of macrophages by influenza virus. *J Virol,* 2000, 74, 5190-7.

Tomiya, N.; Narang, S.; Lee, Y. C. & Betenbaugh, M. J. Comparing N-glycan processing in mammalian cell lines to native and engineered lepidopteran insect cell lines. *Glycoconj J,* 2004, 21, 343-60.

Kyte, J.; Doolittle RF. A simple method for displaying the hydropathic character of a protein. *J Mol Biol* 157, 105, 1982.

What is claimed is:

1. A system for the heterologous expression of a viral protein or a fragment thereof, wherein the viral protein or fragment thereof is from a virus being pathogenic for human and/or animal, said system comprising a) a ciliate host cell, b) at least one nucleic acid encoding for a viral protein, or a fragment thereof, and c) a promoter operably linked to said nucleic acid.

2. The system according to claim 1, further comprising d) a signal sequence operably linked to said nucleic acid, which signal sequence accounts for the secretion of the viral protein or the fragment thereof, encoded by the said nucleic acid, into the extracellular medium.

3. The system according to claim 1, characterized in that the said viral protein is a virus surface protein.

4. The system of claim 1, wherein the ciliate host cell is a member of the family Tetrahymenidae.

5. The system of claim 1, wherein the viral protein is a viral fusion protein.

6. The system of claim 1, wherein the viral protein, or the fragment thereof, encoded by said nucleic acid, is devoid of at least one hydrophobic domain, or a fraction thereof.

7. The system of claim 5, wherein the viral protein is selected from the group consisting of Class I, Class II and Class III viral fusion protein.

* * * * *